(12) United States Patent
Biondi et al.

(10) Patent No.: US 7,334,578 B2
(45) Date of Patent: *Feb. 26, 2008

(54) SYSTEM FOR AUTOMATICALLY WEANING A PATIENT FROM A VENTILATOR, AND METHOD THEREOF

(75) Inventors: James W. Biondi, North Haven, CT (US); Nancy Lockhorn, Hamden, CT (US); Robert Reynolds, New Haven, CT (US)

(73) Assignee: Cardiopulmonary Corporation, Milford, CT (US)

(*) Notice: Subject to any disclaimer, the term of this patent is extended or adjusted under 35 U.S.C. 154(b) by 4 days.

This patent is subject to a terminal disclaimer.

(21) Appl. No.: 11/389,823

(22) Filed: Mar. 27, 2006

(65) Prior Publication Data

US 2006/0162727 A1 Jul. 27, 2006

Related U.S. Application Data

(63) Continuation of application No. 10/716,896, filed on Nov. 17, 2003, now Pat. No. 7,017,574, which is a continuation of application No. 10/260,796, filed on Sep. 30, 2002, now Pat. No. 6,668,829, which is a continuation of application No. 09/767,173, filed on Jan. 22, 2001, now Pat. No. 6,463,930, which is a continuation-in-part of application No. 09/660,820, filed on Sep. 13, 2000, now Pat. No. 6,584,973, which is a continuation of application No. 09/045,461, filed on Mar. 20, 1998, now Pat. No. 6,158,432, which is a continuation-in-part of application No. 08/569,919, filed on Dec. 8, 1995, now Pat. No. 5,931,160.

(51) Int. Cl.
 A61M 16/00 (2006.01)

(52) U.S. Cl. ............... 128/204.23; 128/204.18

(58) Field of Classification Search ........... 128/200.24, 128/204.18, 204.21, 204.22, 204.23, 204.26, 128/205.23, 207.14, 898; 600/529, 538, 600/300, 301

See application file for complete search history.

(56) References Cited

U.S. PATENT DOCUMENTS

| | | |
|---|---|---|
| 3,212,496 A | 10/1965 | Preston |
| 3,741,208 A | 6/1973 | Jonsson et al. |
| 3,835,845 A | 9/1974 | Maher |
| 3,923,055 A | 12/1975 | Hammacher |
| 3,961,627 A | 6/1976 | Ernst et al. |
| 3,972,327 A | 8/1976 | Ernst et al. |
| 3,976,064 A | 8/1976 | Wood et al. |
| 4,016,871 A | 4/1977 | Schiff |
| 4,036,221 A | 7/1977 | Hillsman et al. |
| 4,050,458 A | 9/1977 | Friend |
| 4,141,356 A | 2/1979 | Smargiassi |

(Continued)

FOREIGN PATENT DOCUMENTS

DE 2 348 582 11/1973

(Continued)

OTHER PUBLICATIONS

Adult Star Ventilator "Adult Star Ventilator Operating Instructions" *Adult Star Ventilator.*

(Continued)

*Primary Examiner*—Teena K. Mitchell
(74) *Attorney, Agent, or Firm*—Kirkpatrick & Lockhart Preston Gates Ellis LLP

(57) ABSTRACT

A patient ventilator system for automatically weaning a patient from a ventilator.

14 Claims, 16 Drawing Sheets

U.S. PATENT DOCUMENTS

| | | | |
|---|---|---|---|
| 4,163,450 A | 8/1979 | Kirk et al. | |
| 4,176,663 A | 12/1979 | Hewlett | |
| 4,204,524 A | 5/1980 | Martin et al. | |
| 4,256,100 A | 3/1981 | Levy et al. | |
| 4,281,651 A | 8/1981 | Cox | |
| 4,323,064 A | 4/1982 | Hoenig et al. | |
| 4,340,044 A | 7/1982 | Levy et al. | |
| 4,413,632 A | 11/1983 | Schlessinger et al. | |
| 4,417,573 A | 11/1983 | De Vries | |
| 4,424,806 A | 1/1984 | Newman et al. | |
| 4,444,201 A | 4/1984 | Itoh | |
| 4,448,192 A | 5/1984 | Stawitcke et al. | |
| 4,456,008 A | 6/1984 | Clawson et al. | |
| 4,459,982 A | 7/1984 | Fry | |
| 4,546,770 A | 10/1985 | Schlessinger et al. | |
| 4,637,385 A | 1/1987 | Rusz | |
| 4,676,232 A | 6/1987 | Olsson et al. | |
| 4,838,257 A | 6/1989 | Hatch | |
| 4,840,167 A | 6/1989 | Olsson et al. | |
| 4,877,023 A | 10/1989 | Zalkin | |
| 4,917,080 A | 4/1990 | Bayerlein | |
| 4,928,674 A | 5/1990 | Halperin et al. | |
| 4,984,158 A | 1/1991 | Hillsman | |
| 4,986,268 A | 1/1991 | Tehrani | |
| 4,990,894 A | 2/1991 | Loescher et al. | |
| 5,020,516 A | 6/1991 | Biondi et al. | |
| 5,040,529 A | 8/1991 | Zalkin | |
| 5,072,737 A | 12/1991 | Goulding | |
| 5,092,326 A | 3/1992 | Winn et al. | |
| 5,097,424 A | 3/1992 | Ginevri et al. | |
| 5,103,814 A | 4/1992 | Maher | |
| 5,107,831 A | 4/1992 | Halpern et al. | |
| 5,129,390 A | 7/1992 | Chopin et al. | |
| 5,161,525 A | 11/1992 | Kimm et al. | |
| 5,183,038 A | 2/1993 | Hoffman et al. | |
| 5,188,098 A | 2/1993 | Hoffman et al. | |
| 5,271,389 A | 12/1993 | Isaza et al. | |
| 5,299,568 A | 4/1994 | Forare et al. | |
| 5,303,698 A | 4/1994 | Tobia et al. | |
| 5,303,699 A | 4/1994 | Bonassa et al. | |
| 5,309,919 A | 5/1994 | Snell et al. | |
| 5,316,009 A | 5/1994 | Yamada | |
| 5,319,540 A | 6/1994 | Isaza et al. | |
| 5,323,772 A | 6/1994 | Linden et al. | |
| 5,331,995 A | 7/1994 | Westfall et al. | |
| 5,373,842 A | 12/1994 | Olsson et al. | |
| 5,377,671 A | 1/1995 | Biondi et al. | |
| 5,383,449 A | 1/1995 | Forare et al. | |
| 5,390,666 A | 2/1995 | Kimm et al. | |
| 5,400,777 A | 3/1995 | Olsson et al. | |
| 5,402,796 A | 4/1995 | Packer et al. | |
| 5,419,314 A | 5/1995 | Christopher | |
| 5,429,123 A | 7/1995 | Shaffer et al. | |
| 5,433,193 A | 7/1995 | Sanders et al. | |
| 5,438,980 A | 8/1995 | Phillips | |
| 5,515,844 A | 5/1996 | Christopher | |
| 5,520,192 A | 5/1996 | Kitney et al. | |
| RE35,295 E | 7/1996 | Estes et al. | |
| 5,535,738 A | 7/1996 | Estes et al. | |
| 5,540,233 A | 7/1996 | Larsson et al. | |
| 5,549,106 A | 8/1996 | Gruenke et al. | |
| 5,551,418 A | 9/1996 | Estes et al. | |
| 5,558,086 A | 9/1996 | Smith et al. | |
| 5,596,984 A | 1/1997 | O'Mahony et al. | |
| 5,598,838 A | 2/1997 | Servidio et al. | |
| 5,630,411 A | 5/1997 | Holscher | |
| 5,632,270 A | 5/1997 | O'Mahony et al. | |
| 5,660,171 A | 8/1997 | Kimm et al. | |
| 5,664,563 A | 9/1997 | Schroeder et al. | |
| 5,692,497 A | 12/1997 | Schnitzer et al. | |
| 5,740,796 A | 4/1998 | Skog | |
| 5,743,253 A | 4/1998 | Castor et al. | |
| 5,806,513 A | 9/1998 | Tham et al. | |
| 5,862,802 A | 1/1999 | Bird | |
| 5,868,133 A | 2/1999 | DeVries et al. | |
| 5,875,777 A | 3/1999 | Eriksson | |
| 5,878,744 A | 3/1999 | Pfeiffer | |
| 5,881,723 A | 3/1999 | Wallace et al. | |
| 5,915,380 A | 6/1999 | Wallace et al. | |
| 5,915,381 A | 6/1999 | Nord | |
| 5,918,597 A | 7/1999 | Jones et al. | |
| 5,927,274 A | 7/1999 | Servidio et al. | |
| 5,931,159 A | 8/1999 | Suzuki et al. | |
| 5,931,160 A | 8/1999 | Gilmore et al. | |
| 5,931,162 A | 8/1999 | Christian | |
| 5,937,853 A | 8/1999 | Ström | |
| 5,957,130 A | 9/1999 | Krahbichler et al. | |
| 6,000,396 A | 12/1999 | Melker et al. | |
| 6,015,388 A | 1/2000 | Sackner et al. | |
| 6,024,089 A | 2/2000 | Wallace et al. | |
| 6,029,664 A | 2/2000 | Zdrojkowski et al. | |
| 6,076,523 A | 6/2000 | Jones et al. | |
| 6,095,139 A | 8/2000 | Psaros | |
| 6,148,814 A | 11/2000 | Clemmer et al. | |
| 6,158,432 A | 12/2000 | Biondi et al. | |
| 6,158,433 A | 12/2000 | Ong et al. | |
| 6,182,667 B1 | 2/2001 | Hanks et al. | |
| 6,305,372 B1 | 10/2001 | Servidio | |
| 6,370,419 B1 | 4/2002 | Lampotang et al. | 600/427 |
| 6,390,091 B1 | 5/2002 | Banner et al. | 128/204.21 |
| 6,463,930 B2 | 10/2002 | Biondi et al. | |
| 6,526,970 B2 | 3/2003 | DeVries et al. | 128/204.21 |
| 6,584,973 B1 | 7/2003 | Biondi et al. | |
| 6,668,829 B2 | 12/2003 | Biondi et al. | |
| 6,814,074 B1 | 11/2004 | Nadjafizadeh et al. | 128/204.23 |
| 7,017,574 B2 * | 3/2006 | Biondi et al. | 128/204.21 |

FOREIGN PATENT DOCUMENTS

| | | |
|---|---|---|
| EP | 0 182 722 | 5/1986 |
| EP | 0 342 443 | 5/1988 |
| EP | 0 274 996 | 7/1988 |
| EP | 0 993 841 A1 | 4/2000 |
| FR | 2729084 | 12/1995 |
| GB | 2 162 430 A | 2/1986 |
| NL | 8 801 322 | 12/1989 |
| WO | 92/11054 | 7/1992 |
| WO | 92/11054 A | 7/1992 |
| WO | 96/17641 A | 6/1996 |
| WO | 97/20592 A | 6/1997 |
| WO | 99/47200 A | 9/1999 |
| WO | 00/45880 A | 8/2000 |

OTHER PUBLICATIONS

Bear Medical Systems, Inc. "Bear 5 Medical Ventilator Instruction Manual" *Bear Medical Systems, Inc.* (1985).

Brochard et al., "Comparison of Three Methods of Gradual Withdrawal from Ventilatory Support during Weaning from Mechanical Ventilation," *Am. J. Resp. Crit. Care Med.* (1994), vol. 150, pp. 896-903.

Dries, "Weaning from Mechanical Ventilation," *Journal of Trauma: Injury, Infection, and Crit. Care*, (1997), vol. 43, No. 2, pp. 372-384.

East, T.D., "The Ventilators of the 1990's", Respiratory Care 35: 232-240 (1990).

Esteban et al., "A Comparison of Four Methods of Weaning Patients from Mechanical Ventilation," *N.E. Journal of Med.*, (1995) vol. 332, No. 6, pp. 345-350.

Fontes et al., "Early Extubation Following Cardiac Surgery: Is the Clock Running out on the Elderly?," Cardiopulmonary Corp., Abstract: 1997 American Society for Anesthesiology (1 pg.).

Fontes, et al., "Is Computer-Driven Weaning from Mechanical Ventilation Superior to Clinician-Directed Weaning Following Cardiac Surgery?," Cardiopulmonary Corp., Abstract: 1997 American Society of Cardiovascular Anesthesiology (1 pg.).

Fontes et al., "Does Automated Weaning from Mechanical Ventilation Following Cardiac Surgery Increase the Incidence of Adverse Cardiopulmonary Events?," Cardiopulmonary Corp., Abstract: 1998 Society of Cardiovascular Anesthesiology (1 pg.).

Hamilton Medical "Veolar Operator's Manual" *Hamilton Medical* (Jul. 1988).

Hitchin, J., "Computerized Pulmonary Diagnostics for Infants and Children" *Biomedical Business International* Section 7: 1-3/24 (May 23, 1990).

International Search Report for PCT/US02/01716.

Kollef et al., "A randomized, controlled trial of protocol-directed versus physician-directed weaning from mechanical ventilation." *Crit. Care Med*. (1997) vol. 25, No. 4, pp. 567-574.

Noack, G., M.D., "Ventilatory Treatment of Neonates and Infants" *Siemens* (Apr. 1993).

Puritan Bennett "Puritan Bennett 7200 Series Ventilator, Options, and Accessories—Operation's Manual—Part No. 22300A" *Marketing Communications Department—Puritan-Bennett Corporation* 1-6/9 (Sep. 1990).

Sanborn, W.G., "Ventilation in the Information Age", presented at the Product Opportunities in Critical Care Medicine, Puritan-Bennett Corporation, Carlsbad, CA., May 18, 1989.

Scalise et al., "Comparison of the Average Operating Airway Pressures of the Puritan-Bennett 7200 Ventilator and the Venturi Ventilator in Patients Undergoing Weaning from Prolonged Mechanical Ventilators," Cardiopulmonary Corp., Abstract: 2000 Society for Critical Care Medicine (1 pg.).

Scalise et al., "Comparison of Two Weaning Strategies in Patients Undergoing Prolonged Mechanical Ventilation," Cardiopulmonary Corp., Abstract: 2000 American College of Chest Physicians (1 pg.).

Siemens "Servo Ventilator 300 Service Manual—Preliminary" *Siemens* (1991).

Siemens "Servo Ventilator 900C Operating Manual" *Siemens*.

Wallis et al., "Mechanical Heart-lung intraction with positive end-expiratory pressure", J. Appl. Physiol; Respirat. Environ. Exercise Physiol. 54: 1039-1047 (1983).

\* cited by examiner

IF ((FLOW SLOPE INCREASING)　　　　　　　　　(STEP 300)
AND (PRESSURE SLOPE DECREASING)
  THEN (ADD INHALED VOLUME TO
    TO EVENT VOLUME = (VOLUME - BASELINE))
      ELSE (ADD (0) TO EVENT
        VOLUME = (VOLUME-BASELINE))

IF (EVENT VOLUME > TRIGGER VOLUME)　　　　(STEP 310)
  THEN (TRIGGER FLAG = YES)

IF (TRIGGER FLAG = YES)　　　　　　　　　　　(STEP 320)
  THEN ((IF TIME > 200mSEC) THEN (TRIGGER FLAG = NO)
    ELSE (ADD TO VOLUME = (VOLUME - BASELINE)))

IF (VOLUME > TRIGGER VOLUME)　　(STEP 330)
  THEN (INITIATE BREATH))
    ELSE (DO NOT INITIATE BREATH)

FIG. 6

SYSTEM FOR AUTOMATICALLY WEANING A PATIENT FROM A VENTILATOR, AND METHOD THEREOF

CROSS REFERENCE TO RELATED APPLICATION

This application is a continuation of U.S. Ser. No. 10/716,896, filed Nov. 17, 2003, now issued as U.S. Pat. No. 7,017,574, which is a continuation of U.S. Ser. No. 10/260,796, filed Sep. 30, 2002, now issued as U.S. Pat. No. 6,668,829, which is a continuation of U.S. Ser. No. 09/767,173, filed Jan. 22, 2001, now issued as U.S. Pat. No. 6,463,930, which is a continuation-in-part of U.S. Ser. No. 09/660,820, filed Sep. 13, 2000, now issued as U.S. Pat. No. 6,584,973, which is a continuation of U.S. Ser. No. 09/045,461, filed Mar. 20, 1998, now issued as U.S. Pat. No. 6,158,432, which is a continuation-in-part of U.S. Ser. No. 08/569,919, filed Dec. 8, 1995, now issued as U.S. Pat. No. 5,931,160.

FIELD OF THE INVENTION

The invention relates generally to the field of medical ventilators or, more specifically, to the control of such ventilators.

BACKGROUND OF THE INVENTION

A medical ventilator delivers gas to a patient's respiratory tract and is often required when the patient is unable to maintain adequate ventilation. Mechanical ventilation is the single most important therapeutic modality in the care of critically ill patients. Known ventilators typically include a pneumatic system that delivers and extracts gas pressure, flow and volume characteristics to the patient and a control system (typically consisting of knobs, dials and switches) that provides the interface to the treating clinician. Optimal support of the patient's breathing requires adjustment by the clinician of the pressure, flow, and volume of the delivered gas as the condition of the patient changes. Such adjustments, although highly desirable, are difficult to implement with known ventilators because the control system demands continuous attention and interaction from the clinician.

Further, patients requiring ventilatory assistance must overcome airway resistance in the breathing circuit during exhalation. This resistance, combined with the stiffness of the lungs and the thoracic cage under certain pathological conditions, imposes a significant workload upon a patient whose reserves may already be compromised by underlying disease processes.

SUMMARY OF THE INVENTION

The invention relates to a medical mechanical ventilator device adapted for use in weaning a patient from mechanical ventilation. In one embodiment, the device measures the patient's minute volume, breath frequency, and detects a patient's spontaneous breath. The device compares the patient's minute volume and the patient breath rate to a predetermined minute volume and a predetermined breath rate entered by a clinician. In a pressure support mode, the device decreases patient pressure support level if the patient's spontaneous breathing rate falls within the predetermined range of breathing and the patient's minute volume exceeds the predetermined minute volume. In one embodiment, the patient's spontaneous breathing rate and the patient's minute volume is determined on a breath-by-breath basis. For the purposes of this invention, intrabreath is defined as within the period of one breath cycle, and interbreath is defined as within the period of at least two breaths.

In another embodiment, the invention is a ventilator system adapted for use in weaning a patient from mechanical ventilation. The ventilator system comprises a pressure source in communication with the patient's respiratory system to provide pressure support to the patient. The device further comprises a breath frequency monitor, a minute volume flow meter, an input device, and a data processing unit. The data processing unit compares the patient's breathing frequency and patient's minute volume to the breathing frequency and minute volume entered by the clinician. Pressure support is adjusted by the ventilator on an intrabreath or interbreath basis.

BRIEF DESCRIPTIONS OF THE DRAWINGS

Figure 6A:
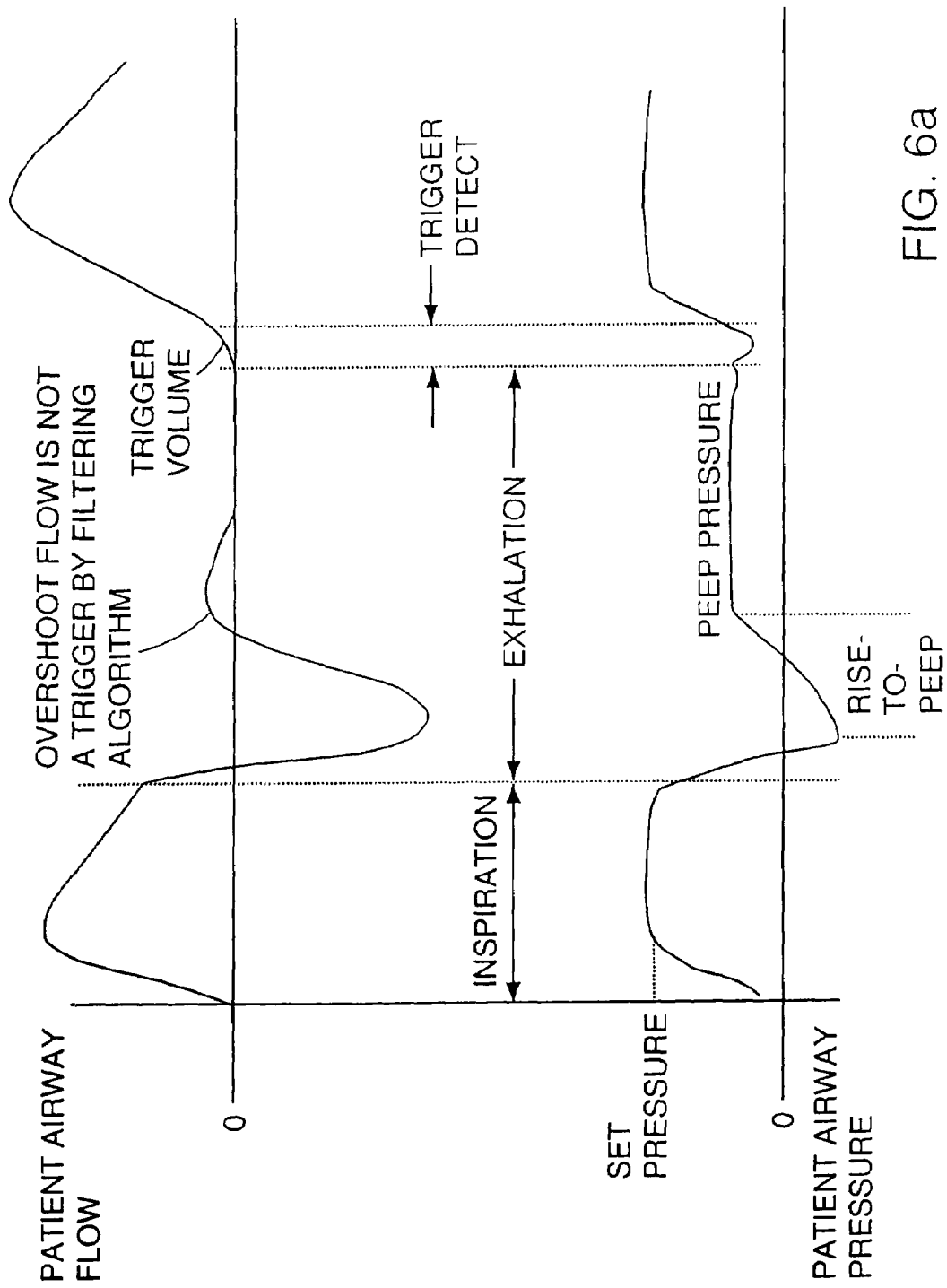
FIG. 6 is psuedocode of an embodiment of a triggering algorithm used by the ventilator of the invention.

FIG. 6*a* is a pressure and flow diagram of the patient airway gas flow and patient airway pressure used by the algorithm of FIG. 6 to determine patient ventilation triggering.

Figure 7:
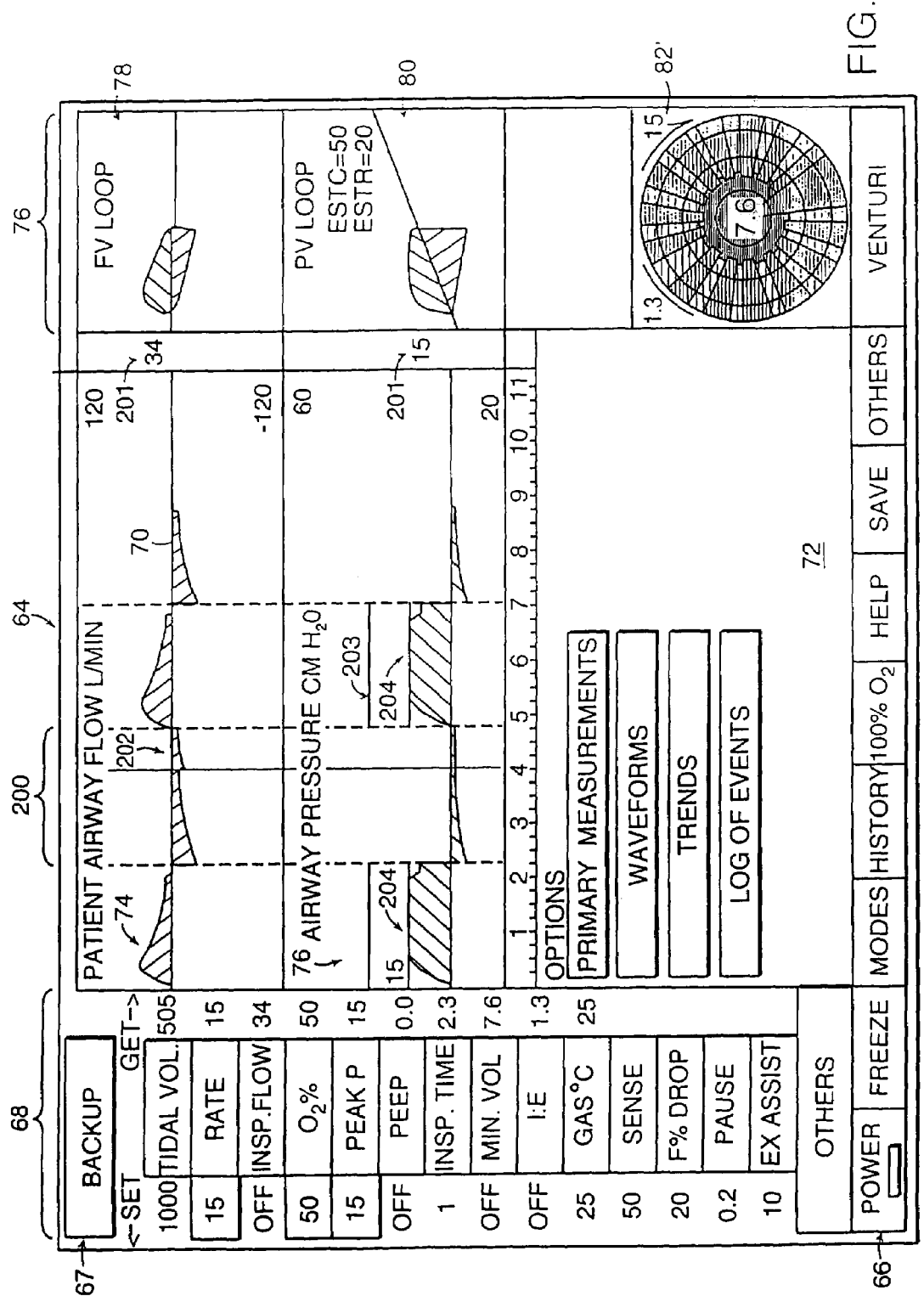

FIG. 7 is an illustration of a display screen when the ventilator control system is in the operational mode.

Figure 8:
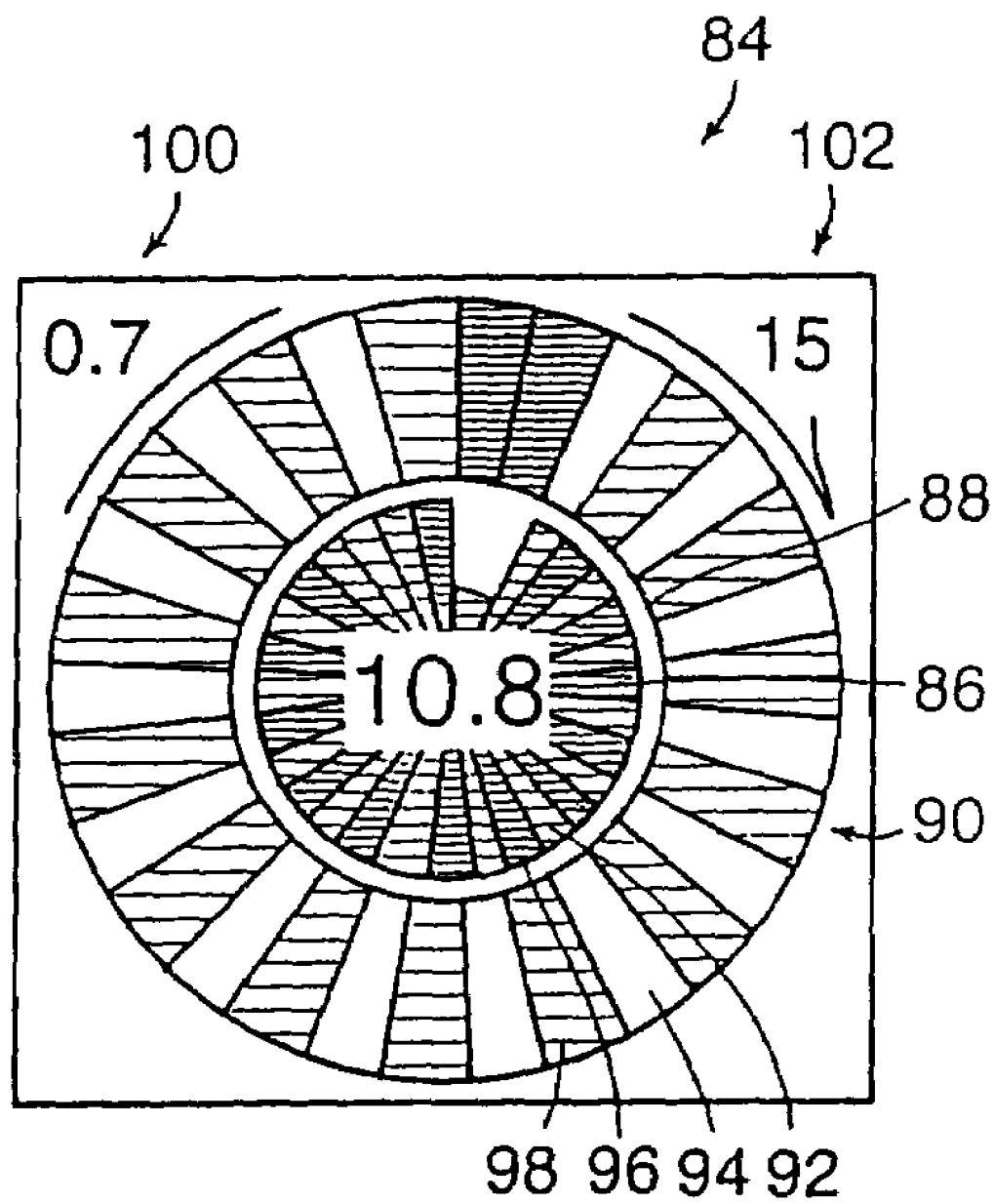

FIG. 8 is an illustration of a section of the display screening showing a minute volume wheel.

Figure 9:
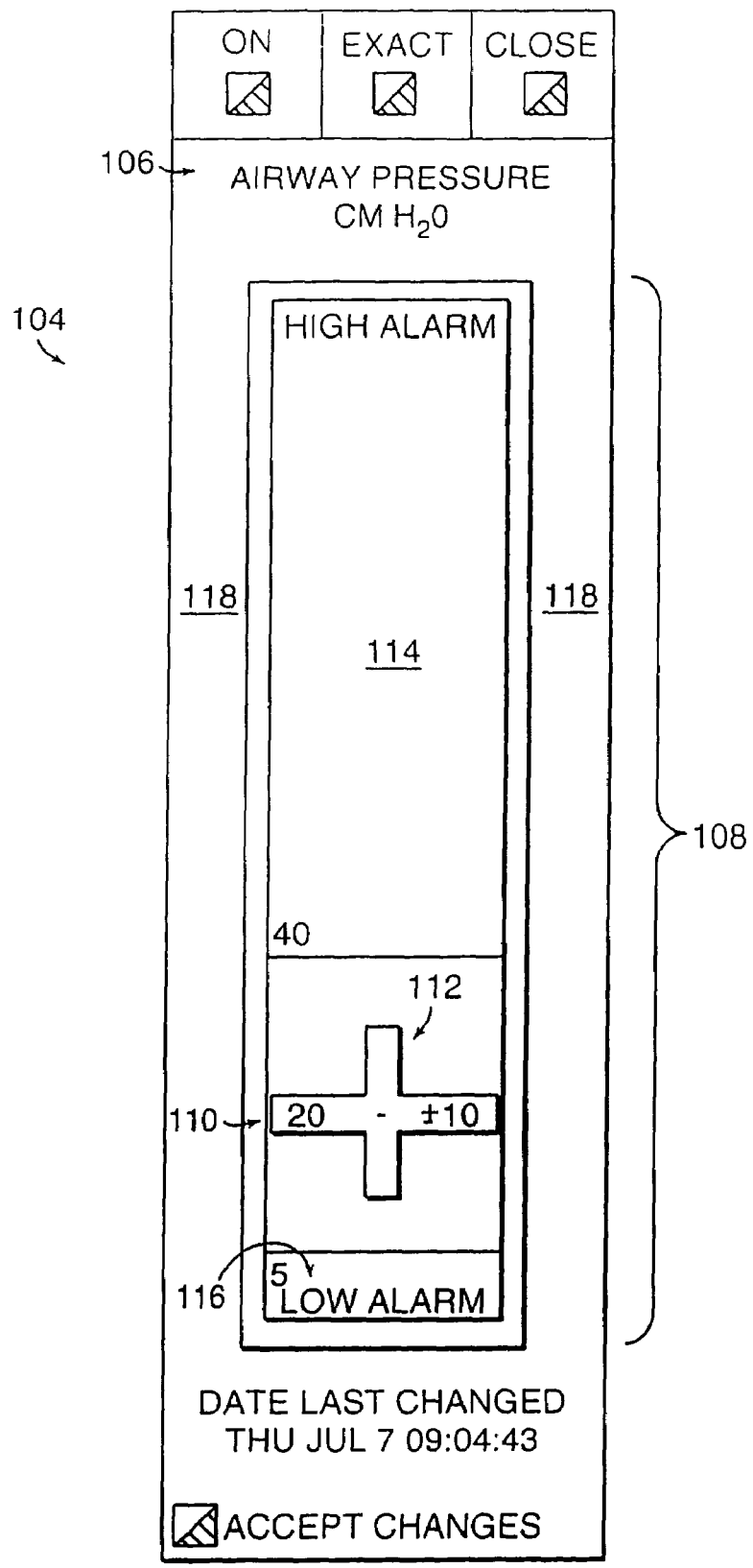

FIG. 9 is an illustration of a section of the display screening showing a control slider.

Figure 10:
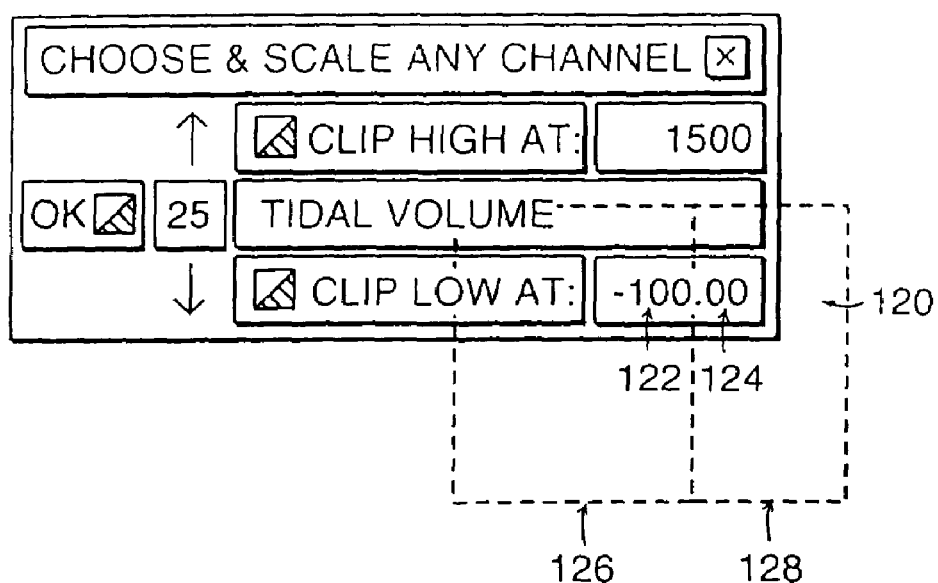

FIG. 10 is an illustration of a section of the display screening showing a numerical controller.

Figure 11:
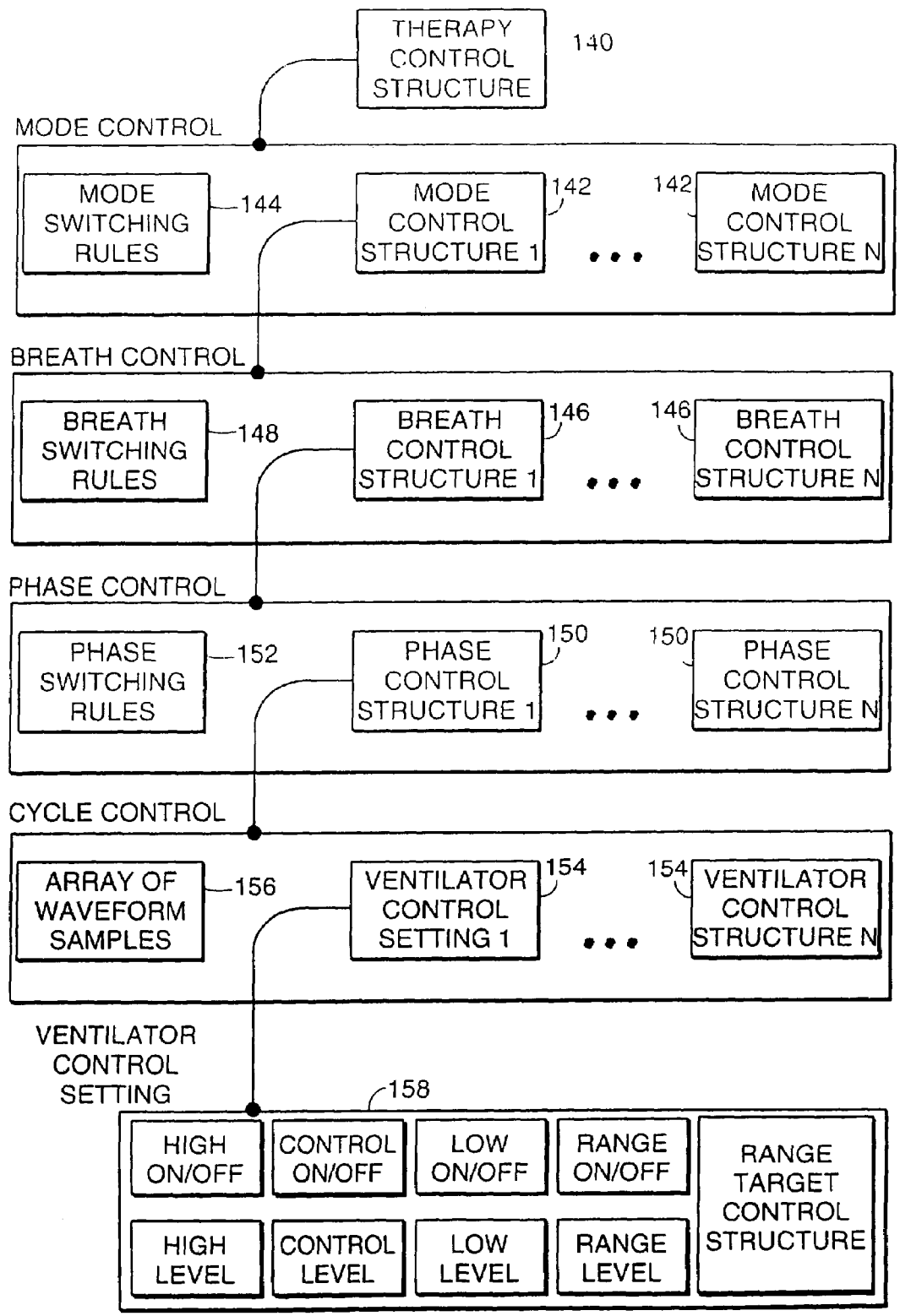

FIG. 11 is a flow chart of the data structure hierarchy employed by the ventilator control system.

Figure 12:
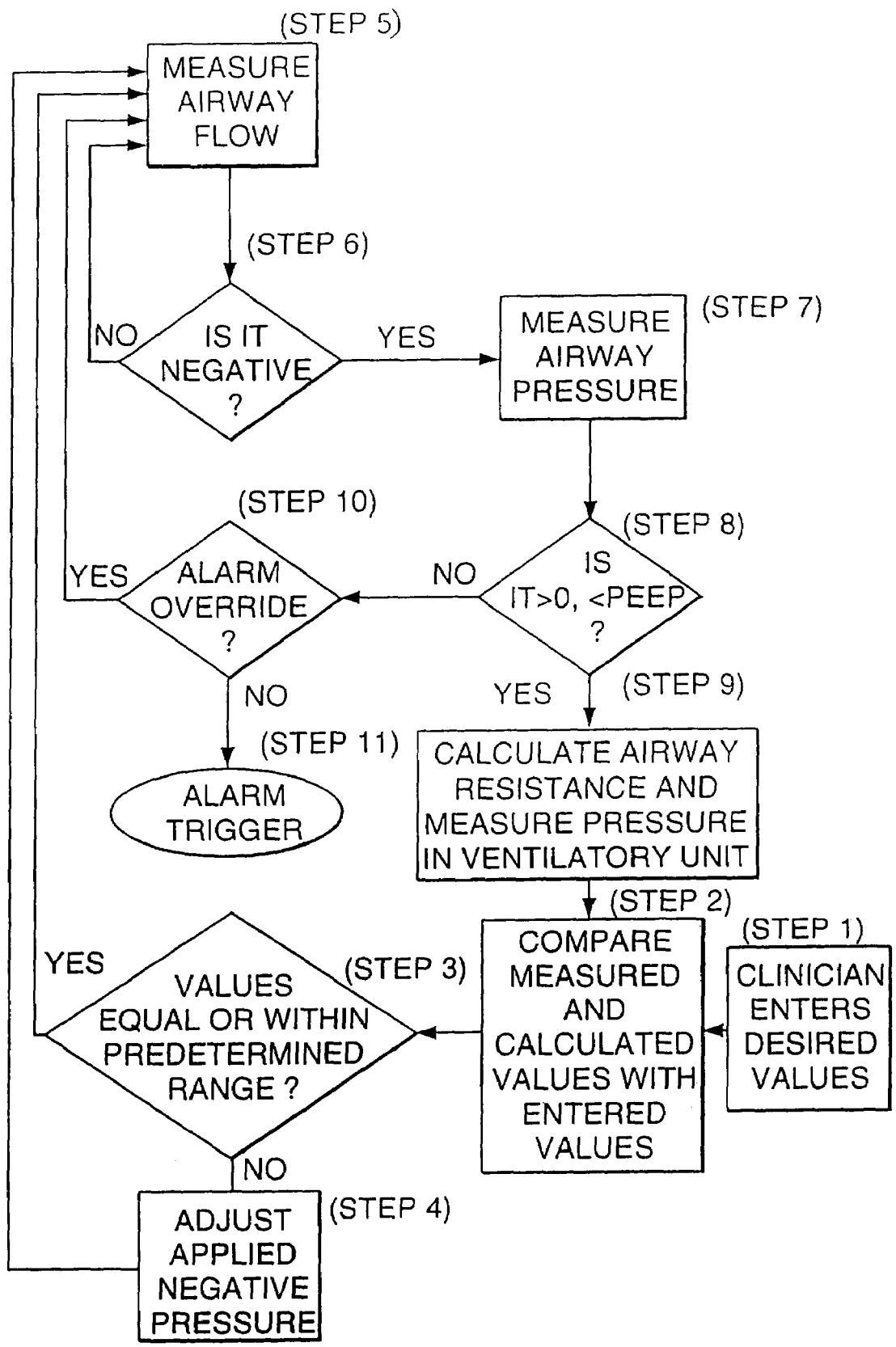

FIG. 12 is an embodiment of a flow chart of an exhalation assist algorithm executed by an embodiment of the invention.

Figure 13:
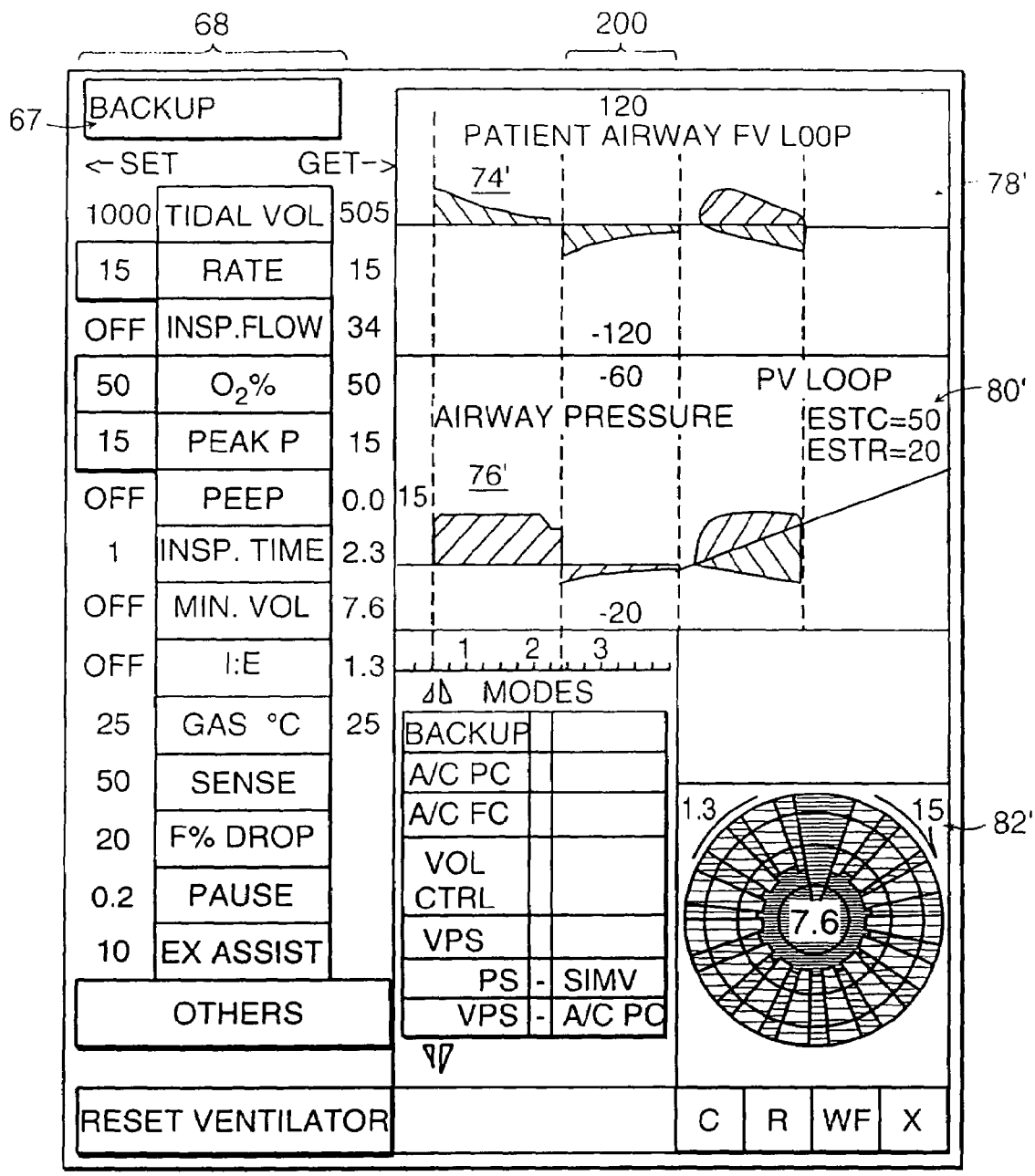

FIG. 13 is an illustration of a simulation mode display screen for the ventilator control system.

Figure 15:
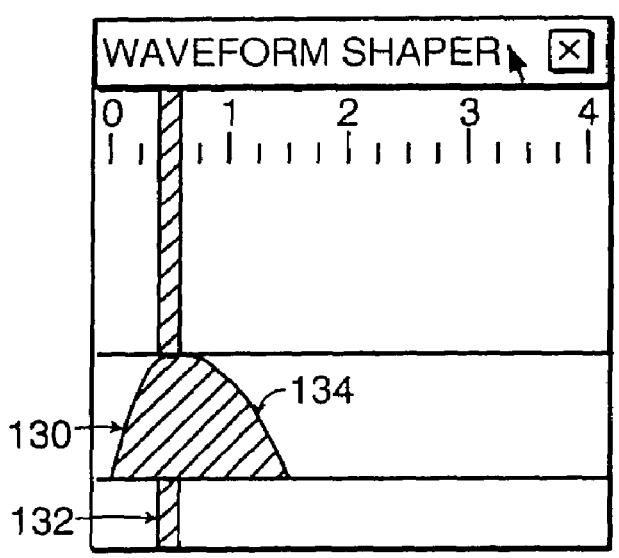
Figure 14:
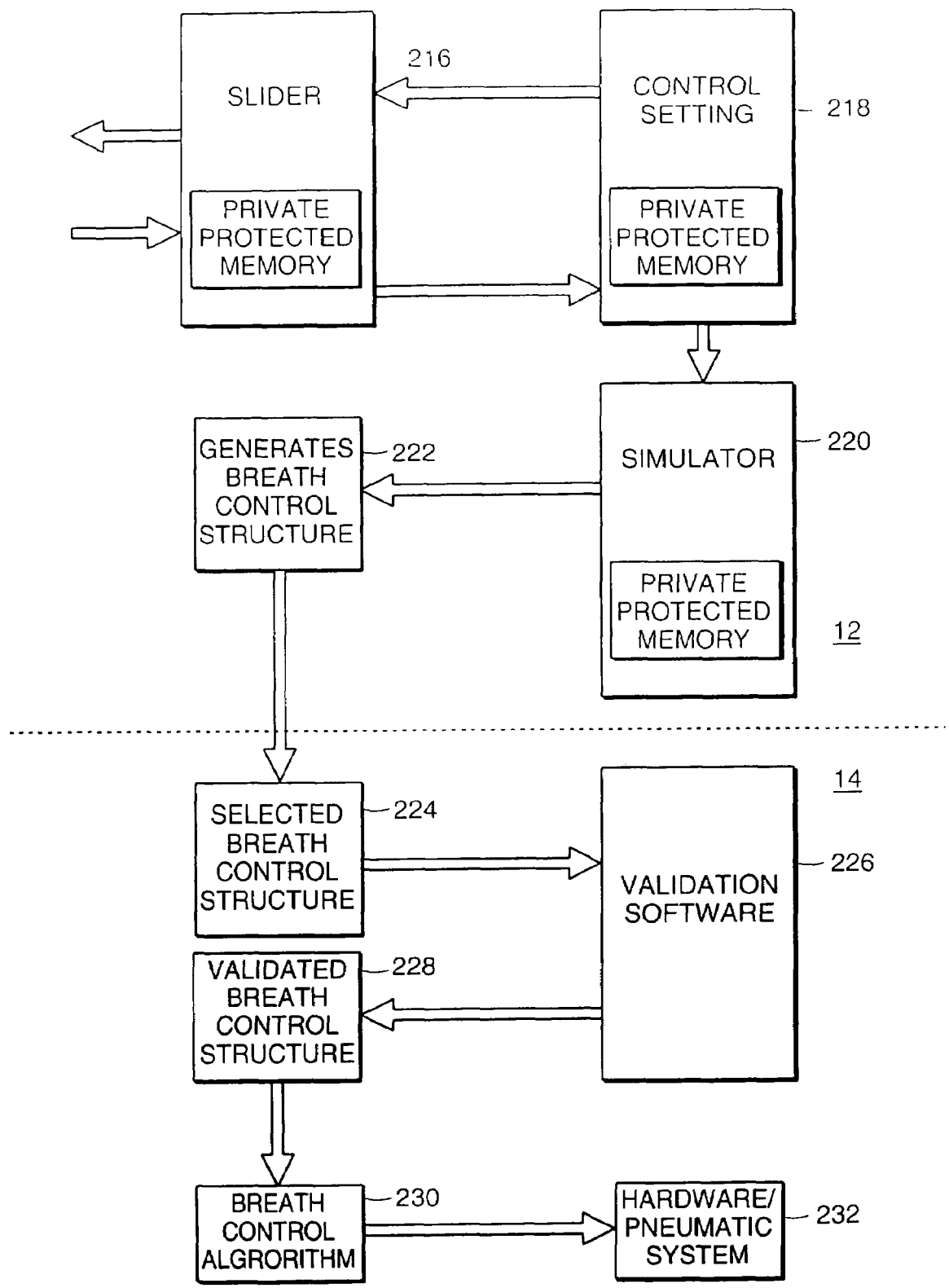

FIG. 14 is a functional block diagram of the simulator portion of the ventilator control system FIG. 15 is an illustration of a section of the display screening showing a waveform shaper.

Figure 16:
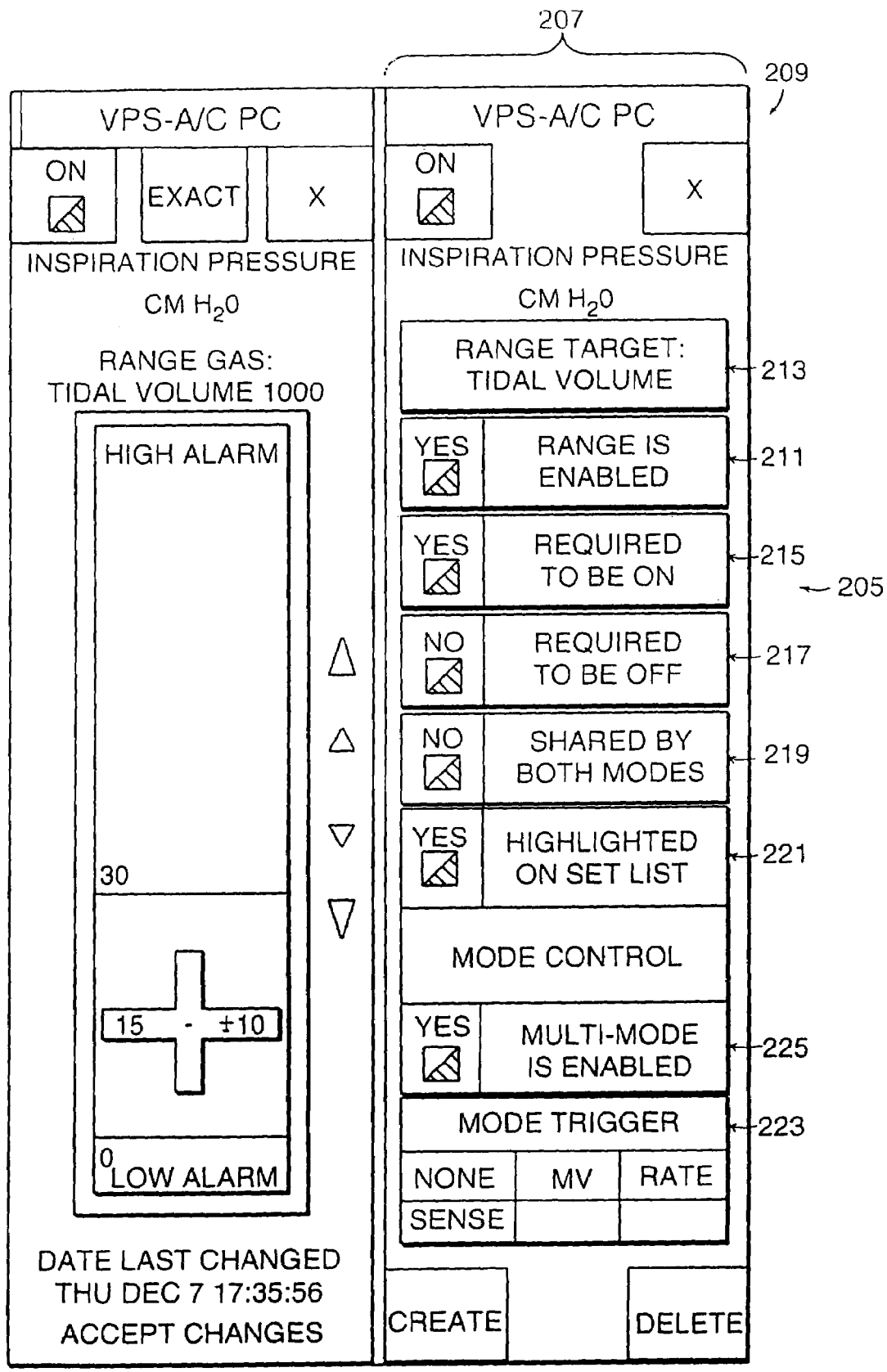

FIG. 16 is an illustration of a therapy programming screen for the ventilator control system.

Figure 17:
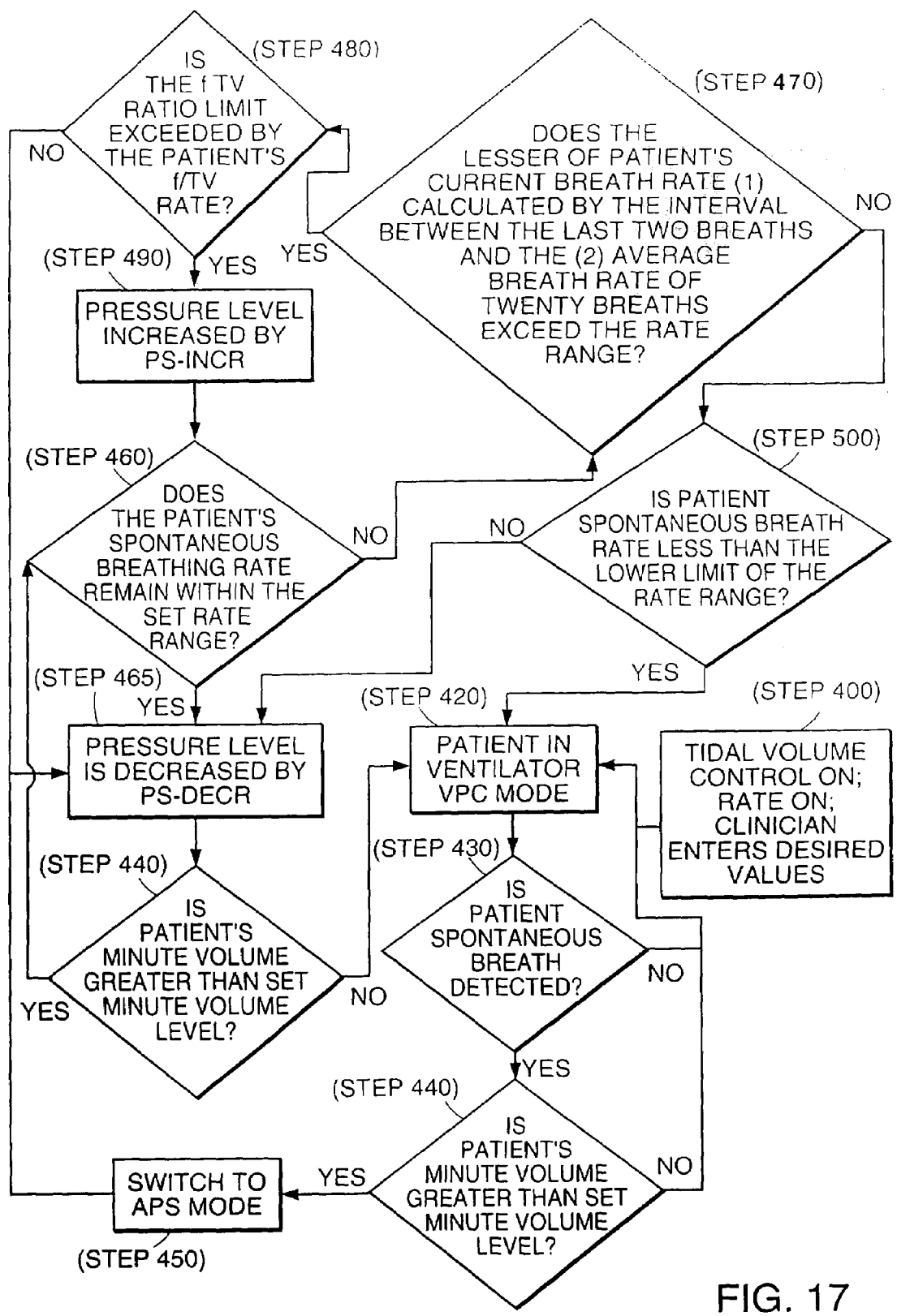

FIG. 17 is a flow chart for automatic weaning of a patient from a ventilator according to an embodiment of the invention.

DETAILED DESCRIPTION OF THE INVENTION

1. Ventilator Control System—The invention features a ventilator control system for controlling a ventilator pneumatic system in a medical ventilator. The ventilator control system provides a clinician with complete control of a patient's airway flow and pressure throughout the respiratory cycle, and thereby enables the clinician to determine the optimal therapy for the patient. In order to decrease the work of exhalation in this situation, negative pressure can be applied to the exhalation circuit of the patient's ventilator to reduce the resistance to airflow.

Because resistance to airflow is an exponential function of flow, negative pressure must be adjusted to compensate for resistance as increases and decreases in airflow and airway resistance occur. If too much negative pressure is applied to the conducting airways dynamic collapse of the conducting airways can occur and this may result in alveolar gas trapping. Varying the applied negative pressure according to airflow and airway resistance allows maximum assist to be applied during peak expiration, when resistance and work of breathing is greatest. By decreasing the applied negative pressure at lower airflow rates, airway collapse can be averted.

If airway pressure rises above the clinically indicated level of positive end-expiratory pressure (PEEP), the lung will be overpressurized thus the effective airway pressure throughout the expiratory cycle is titrated throughout the expiratory phase under precise algorithmic control. The clinical benefit of a certain PEEP level will be diminished. Thus, the effective airway pressure throughout the expiratory cycle must remain greater than zero and less than PEEP.

Figure 1:
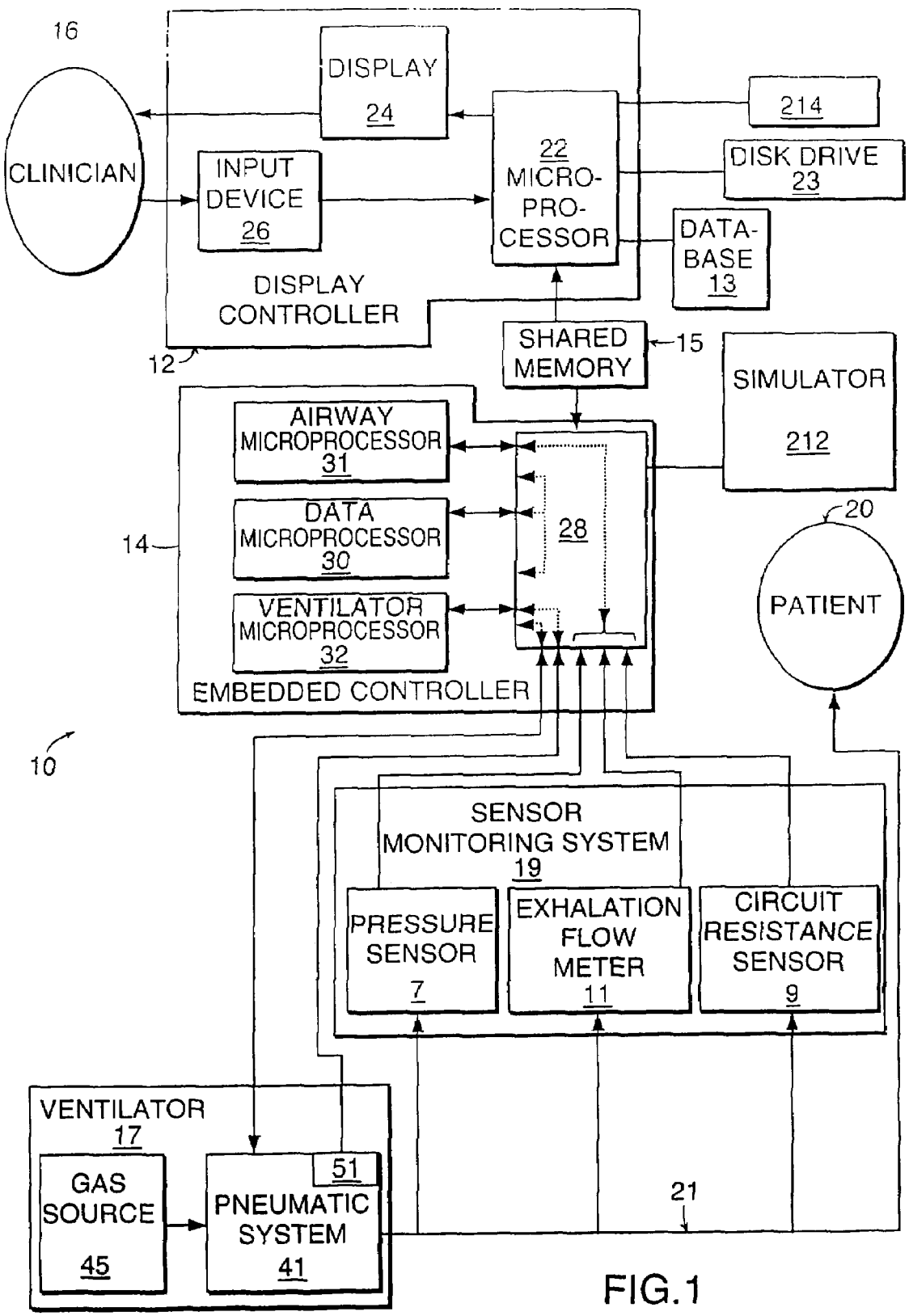
FIG. 1 is a block diagram of an embodiment of a ventilator of the invention.

FIG. 1 is a block diagram of a ventilator including a ventilator control system 10 incorporating the features of the invention. The ventilator control system 10 includes a display controller 12 and an embedded controller 14. The display controller 12 provides an interface to the clinician 16, and the embedded controller 14 provides an interface with a ventilator 17 providing ventilation to a patient 20. The display controller 12 and the embedded controller 14 each include memory (not shown) and are electrically coupled via a shared memory interface 15. Data from the display controller 12 and the embedded controller 14 are stored in a database 13.

A sensor monitoring system 19, including an exhalation flowmeter 11 a circuit resistance sensor 9 and a pressure sensor 7 in communication with the airway 21, provide signals to a embedded controller 14 relating to airway pressure, flow and resistance. These measured values are stored in a database 13. These values are also compared with values preselected by a user by way of the embedded controller 14 to calculate the amount of negative pressure to be generated in the ventilator 17 in order to produce an airway pressure greater than zero and less than positive end-expiratory pressure. A pneumatic system 41 regulates the flow of gas delivered from the source of pressurized gas 45 through a Venturi valve within the ventilator 17 to produce this negative pressure. One embodiment of such a pneumatic system 41 is described in U.S. Pat. No. 5,664,563, owned by the assignee of the present invention, incorporated herein by reference. A pressure sensor 51 measures the amount of negative pressure produced within the ventilator 17 and transmits these data to the embedded controller 14. These data are stored in the database 13 and displayed on the display 24 of the display controller 12.

Initially, the clinician 16 enters target values into the system 10 by way of the input device 26 of the display controller 12. Each of these target values is compared with a corresponding current value of ventilatory unit pressure, airway pressure, airway flow and airway resistance by the embedded controller 14. Upon determining that there is a difference between current pressure, flow and resistance values and those values entered by the clinician 16, the embedded controller 14 generates a signal to the pneumatic system 41 so that the pneumatic system 41 changes the amount of negative pressure produced by the ventilator 17. The ventilator 17 is in pneumatic communication with a flexible tubing 21 capable of attachment to a patient 20. The clinician 16 can also directly adjust the pneumatic system 41 by manipulating a plurality of controls on the input device 26 of the display controller 12.

The clinician 16 enters numerical data at the display controller 12 relating to the desired level of airway resistance in the flexible airway tubing 21 or relating to the desired amount of negative pressure in the pneumatic system 41. These entered values signal the pneumatic system 41 to change the amount of negative pressure on a per breath basis within the pneumatic system 41 until the pressure in the pneumatic system 41 or the resistance in the airway tubing 21 equals the value entered by the clinician 16.

The pneumatic system 41 controls gas flow and pressure in the patient's airway using a patient circuit. An electromechanical fresh gas flow control and measurement system provides a metered blend of oxygen and air via a heated, humidified gas delivery system. A high speed pneumatically driven, electronically controlled proportional valve and dual Venturi system provides bi-directional flow and pressure control as described in U.S. Pat. No. 5,664,563 incorporated herein by reference. Pressure 7 and flow 11 sensors provide feedback control of the desired breathing pattern and verify operation within safe limits. The pneumatic and electronic systems and patient circuit are described in extensive detail in commonly assigned patent application Ser. No. 08/352,658, incorporated herein by reference.

The safe performance of the ventilator 10 is enhanced by the redundancy of the two independent display controller 22 and embedded controller 30 processors, which continually check each other's performance via the shared memory interface 15. The embedded controller 14 communicates its status, and that of the patient, to the display controller 12. The embedded controller 14 maintains a non-volatile record of the therapy control structure and continues to operate at the last known good settings if communication becomes lost. The two systems which comprise the ventilator control system 10 give both audible and visual messages when an alarm condition exists, and maintain an alarm history. The systems provide alarms and mandatory patient support upon detection of apnea (i.e., the detected absence of breathing). During operation, both systems perform background tests to detect system faults. The ventilator provides a series of reduced operation modes to provide life support if system capability is compromised.

Figure 2:
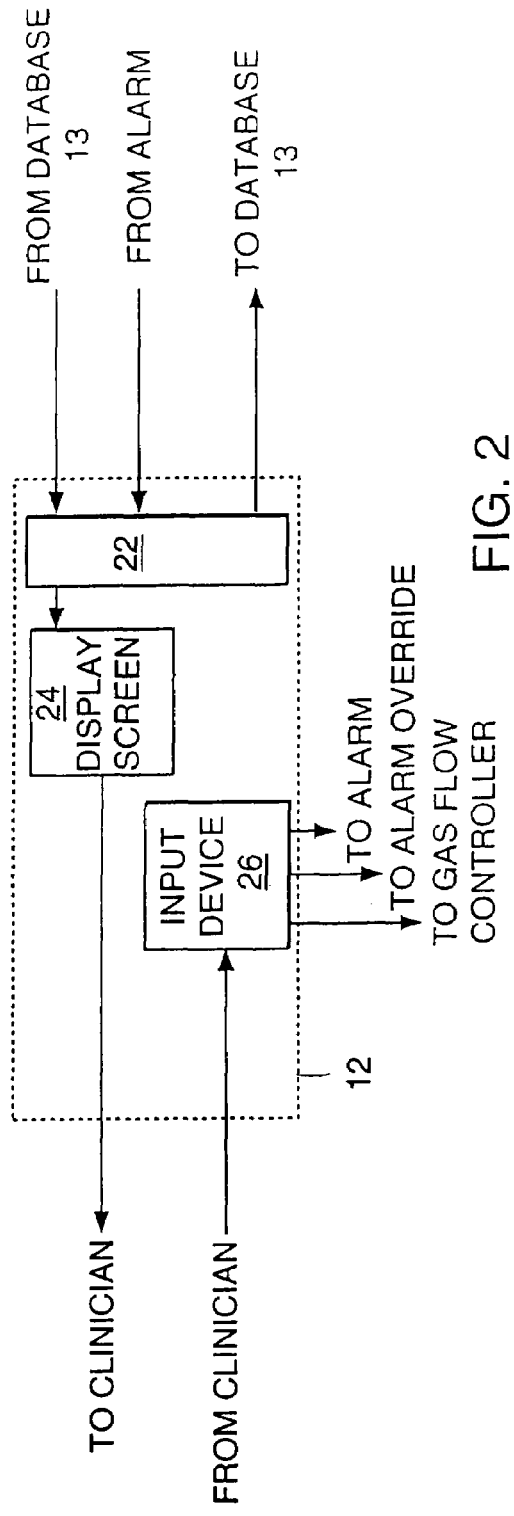
FIG. 2 is a detailed block diagram of a display controller.

In more detail, FIG. 2 is a block diagram of the display controller 12. The display controller 12 includes a processor 22, a display 24 and an input device 26. In one embodiment, the input device 26 is a touchscreen used in conjunction with the display 24. The processor 22 collects input information from the clinician 16, validates the input, creates a therapy control structure from the input information and sends the resulting structure to the embedded controller 14. The therapy control structure is a hierarchical arrangement of similar data structures which includes one or more mode control structures, one or more breath control structures, one or more phase control structures and one or more cycle control structures. Data generated and collected by the processor 22 are stored in the database 13. The display 24 maintains and displays the patient's history in a graphical format which highlights the patient's status. In one embodiment, the display 24 is a CRT. In another embodiment, the display 24 is a flat panel display. More specifically, the display 24 provides a visual indication of the current breath control parameters, alarm and fault conditions, and the current status of the patient's pulmonary system, including gas pressure, flow and volume. In one embodiment, the touchscreen 26 covers the surface of the CRT display 24 and provides a straightforward, highly flexible means to change control settings.

The display controller 12 is a powerful graphics workstation with hardware and software components. In one embodiment, the clinician interacts with the display controller 12 via a color CRT monitor 24 and a touchscreen 26. The display 24 is modified to run from an isolated power supply, and the touchscreen power supply and controller are built in to the monitor. In one embodiment, the processor 22 is included in a single board computer which also includes RAM, an integrated high speed graphics driver, and an integrated dual port memory. The display controller 12 also includes a hard disk drive 23.

While the display controller 12 provides interpretation and decision support information on the display 24, the ventilator 17 does not change any breath control parameters unless directed by the clinician 16. Nevertheless, the display controller 12 provides a flexible user interface with multiple interactive levels, from simple text menus of controls for inexperienced users, to complete visual feedback for clinicians who understand the patient models and can intervene more aggressively and effectively.

Figure 3:
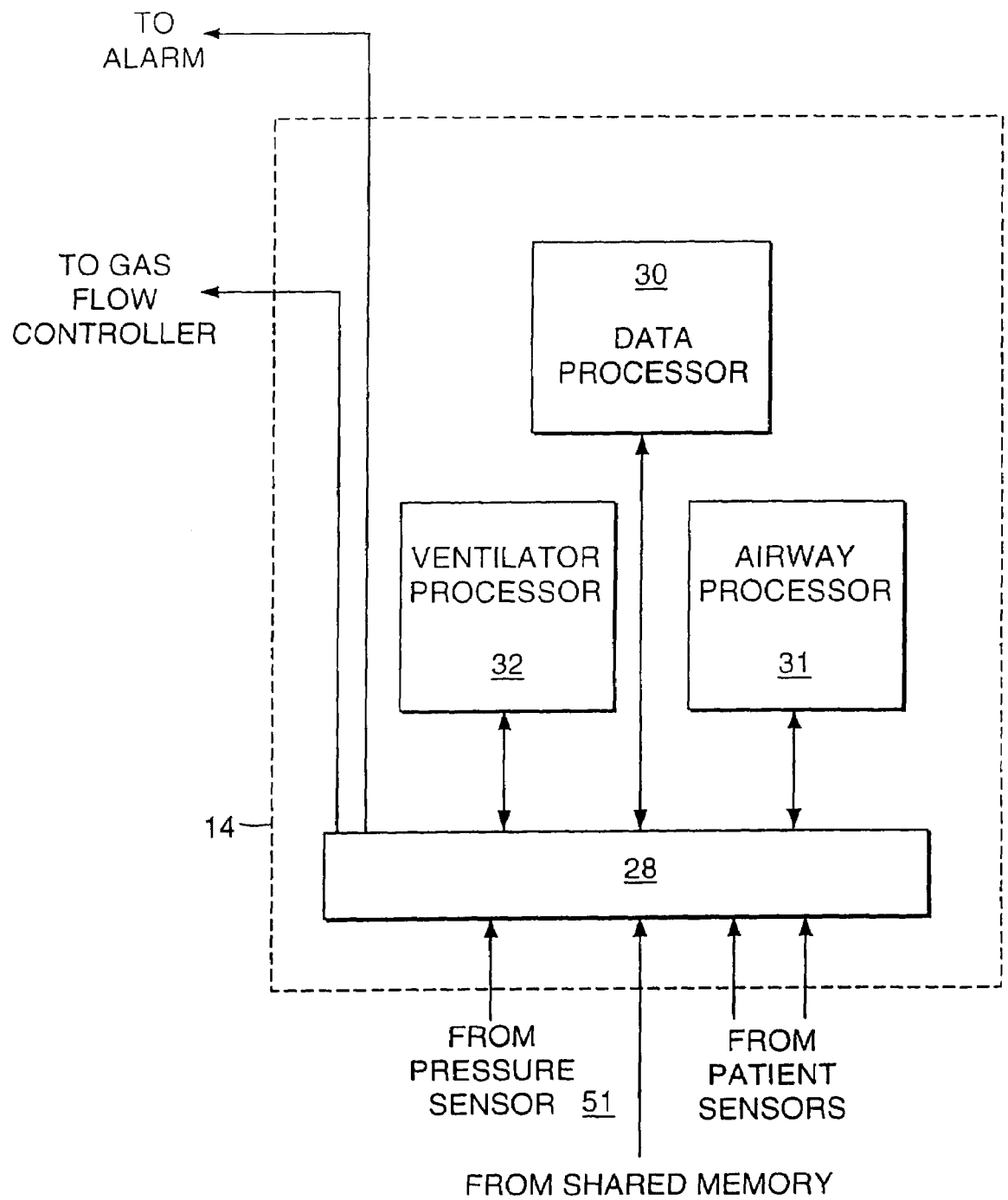
FIG. 3 is a detailed block diagram of an embedded controller.

In more detail, and referring also to FIG. 3 a block diagram of the embedded controller 14 is depicted. In one embodiment, the embedded controller 14 includes a system board 28, a real time data processor 30, a ventilator processor 32 and an airway processor 31. The real time processor 30 manages sensor data collection from the sensor monitoring system 19, processes measured data, performs alarm/fault detection and provides control data to the ventilator 17. The embedded controller 14 further receives data input by the clinician 16 and accesses with the database 13.

A first data processor 31, an airway processor, receives signals from the patient sensor monitoring system 19 relating to airway pressure, flow and resistance. A second data processor 32, a ventilatory unit processor, receives signals from the pressure sensor 51 in communication with the ventilatory pneumatic system 18. Signals from both data processors 31 and 32 are transmitted to a third data processor, a real time data processor 30. This data processor 30 calculates the amount of negative pressure that must be generated by the pneumatic system 41 to change the airway resistance to exhalation. This calculation is made by comparing the data relating to airway pressure, flow and resistance to preselected values and then calculating the change in ventilatory unit negative pressure required to affect the desired change in airway resistance.

Figure 4:
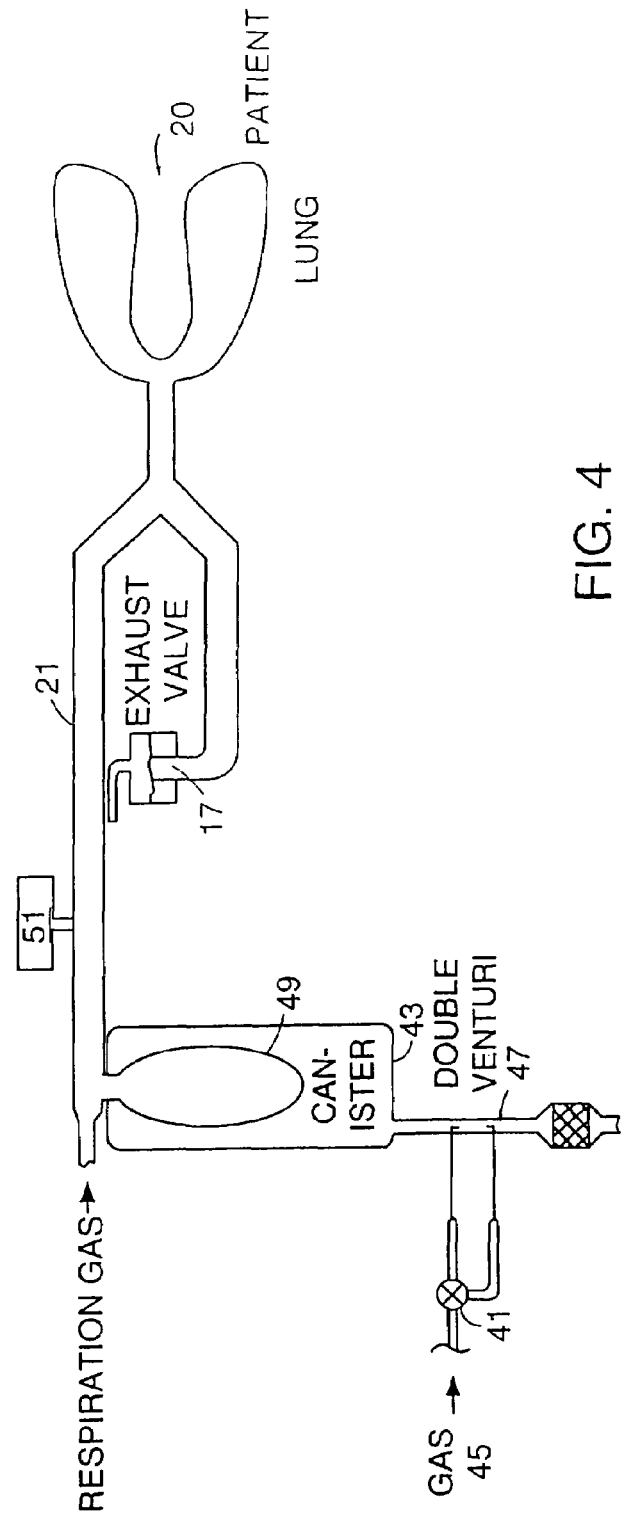
FIG. 4 is a detailed block diagram of a ventilator pneumatic unit.

In more detail, and referring also to FIG. 4, a block diagram of the ventilator 17 in communication with the flexible airway 21 that is the conduit for inhalation from the patient 20 is depicted. The pneumatic system 41 regulates the amount of negative pressure produced within a rigid chamber 43 by adjusting the flow of gas from a source of pressurized gas 45 through a Venturi valve 47. Within the rigid chamber 43 is a flexible canister 49. Negative pressure produced within the rigid chamber 43 is transmitted to the flexible canister 49 and thus to the patient airway 21 which is in pneumatic communication with the flexible canister 49. In this way, negative pressure is applied to the patient airway 21 to assist the patient's exhalation through the canister 49 into the medical ventilator 7. Pressure within the flexible canister 49 is measured by a pressure sensor 51. These data are transmitted to the embedded controller 14.

Figure 5:
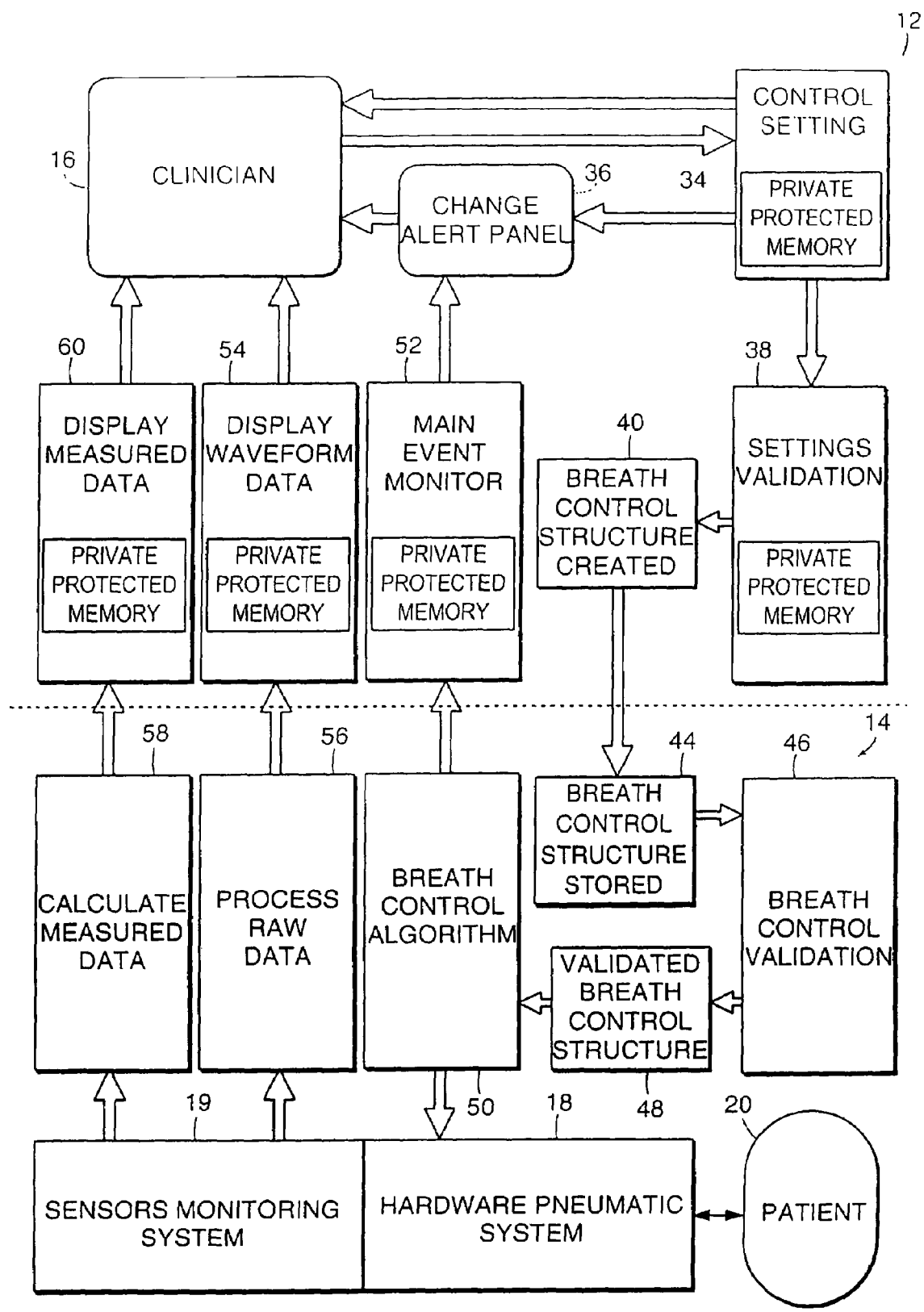
FIG. 5 is a diagram illustrating an embodiment of the adjustment of negative pressure applied to a patient as performed by an embodiment of the invention.

Now referring also to FIG. 5 a detailed functional block diagram of the ventilator control system 10 is depicted. As shown, the clinician 16 manipulates a control setting slider 34 to change or set one or more breath parameters. A change alert panel 36 on the display 24 informs the clinician 16 of the process, from input to implementation, to assure him that his input information is being processed properly. As noted previously, a change to one or more breath parameters will lead to changes in one or more data structures of the therapy control structure hierarchy. It is noted that FIG. 5 provides an example of a breath parameter change which results in a change at the level of the breath control structure. The validation process includes the processor 22 validating 38 the clinician's inputs and creating 40 a breath control structure which is stored in memory. The display controller 12 transmits the breath control structure to the embedded controller 14 and informs the clinician 16 of successful transmission via the change alert panel 36. The embedded controller 14 initially stores 44 the breath control structure in local memory. The embedded controller 14 re-validates 46 the settings within the breath control structure. The embedded controller 14 implements 48 the validated breath control structure 48 using a breath control algorithm 50 and provides signals to the pneumatic system 41 for simultaneously changing one or more control settings at the appropriate time. This process enables the user to change or implement a new therapy so that the therapy delivered to the patient is essentially uninterrupted, and the new therapy is synchronized with the next inspiration. If, however, any step in the process is not completed, the clinician is alerted via the panel 36 to the cause of the error and the process is terminated.

The ventilator control system 10 provides two independent feedback paths to assure the clinician 16 that his setting change has been properly implemented. First, the embedded controller 14 calculates a series of breath monitoring values and sends them to the display controller 12, where the values are displayed 60 contiguous to the desired setting controls. The breath monitoring values can be, for example, set breath rate, measured breath rate, set tidal volume, measured inhaled volume, and measured exhaled volume. The display controller 12 also displays 60 a series of measurements (e.g., peak airway pressure, peak airway flow, and PEEP) from the waveform data both numerically and graphically. Second, the display controller 12 displays 54 the continuous waveforms on the display 24. The waveforms are derived 56 from raw data from the sensors 19, returned from the embedded controller 14 and passed directly to the display 24.

One feature of the ventilator control system 10 is that it can be configured to provide an assisted phase of a breath to the patient 20. As noted previously, the accumulated volume of gas inhaled by the patient as a result of his spontaneous respiratory muscle activity can be monitored. To accomplish this, the sensor monitoring system 19 measures the flow of gas inhaled by the patient 20 at the beginning of the inspiration phase of the breath and integrates the flow to provide the measured volume. The embedded controller 14 compares the measured volume to a trigger volume set by the clinician 16, and adjusts the plurality of controls within the pneumatic system 41 when the measured accumulated volume exceeds the trigger volume to provide an assisted phase of a breath. The embedded controller 14 also may adjust the trigger volume dynamically according to measured patient flow and pressure signals indicating the phase of the respiratory cycle. In particular, the embedded controller 14 may increase the trigger volume set by the clinician 16 during periods of the breath where increases in the pressure at the airway of the patient 20 may be induced by changes in the pneumatic system 41, and not by spontaneous efforts of the patient.

Another feature of the ventilator control system is its ability to distinguish between active inspiratory effort and passive reverse airflow due to the elastic rebound of the chest wall and lungs. The present system is configured such that if the patient's spontaneous inspiratory efforts are being assisted, passive reverse airflow can not erroneously trigger an assisted breath. To accomplish this pressure and flow data provided by the sensor monitoring system 19 are analyzed by the imbedded controller 14 to discriminate between passive airflow and active initiation of inspiration. Specifically, referring to FIGS. 6 and 6a, the clinician sets the trigger volume needed to initiate a breath. The system 10 then determines the baseline pressure and flow for the patient.

As the patient exhales, the system 10 monitors both the patient airway flow and the patient airway pressure. Referring to FIG. 6, if the gas flow is seen to flow into the patient, and the pressure slope is positive, the flow into the patient is considered to be a result of changes in the pneumatic system and no inhalation is triggered (FIG. 6a). If the pressure decreases and the gas flow is into the patient (Step 300), then the total amount of gas inhaled by the patient is measured, and compared to the trigger volume (Step 310).

If the total amount of gas inhaled is greater than the trigger volume and this value has been reached in less than 200 msec, a breath is initiated. If the trigger volume has not been reached and it is taking more than 200 msec, the volume of inhaled gas is continued to be measured until the trigger volume has been reached (Steps 320, 330).

Another feature of the ventilator control system is its ability to compensate for gas flow resistance into and out of the lungs of the patient 20. Using the input device 26, the clinician 16 can set a resistance parameter of the patient's respiratory system to a selected value. Alternatively, the display controller 12 may calculate a value for the gas flow resistance from gas flow and pressure measurements provided by the sensor monitoring system 19. The gas flow resistance is described by the equation:

Gas Flow Resistance=(Inspiration Peak Pressure−End Inspiration Plateau Pressure)/(Inspiration Flow at Peak).

The selected or calculated resistance value is provided to the embedded controller 14 by the display controller 12. The embedded controller 14 adjusts one or more controls of the pneumatic system 41 to compensate for the resistance to flow. The compensation for resistance to flow may be selected to occur during any one or more of the inspiration, exhalation or post-breath phases of a breath. Further, the controls may be adjusted to compensate for different selected or calculated resistance during different phases of a breath.

2. Display Controller—The display controller 12 is an intelligent assistant for the clinician 16. The display controller 12 quickly informs the clinician 16 of the effects of intervention, provides fast, graphical feedback, and presents information in a manner that requires minimal training to understand.

Referring also to FIG. 7 an illustration of a display screen 64 provided by the display controller 12 is depicted. The display controller 12 uses software-generated waveforms and software-generated icons for control and alarms settings. The bottom row of touch sensitive on/off buttons 66 includes: a Power button that controls the ventilator control system; a Freeze button to pause the display; a Modes button to display various modes; a History button to play back a database of historical patient protocols; a 100% $O_2$ button to flush the ventilator with oxygen; Help and Save buttons; and an Others button to display other capabilities.

The left side of the screen includes a list of the publicly available ventilator control settings. The top area displays the current mode of ventilation 67 (e.g., Backup). Below the current mode display, each row in the list has three columns. The left column is the current set value. If a row in the left column is inactive, it displays an OFF indication. Important current set values are highlighted. The middle column is a touch sensitive display showing the abbreviated title of the setting. The right column is the actual value of the setting as measured during the previous breath. If the actual value exceeds an alarm limit, the exceeded value turns red and a large alarm message is displayed on the screen. By touching a row, a control slider (not shown) appears on the right side of the screen. The control slider enables the clinician to change various parameters (e.g., alarm levels, control settings) and is described in detail below.

The middle area of the display screen is divided into top and bottom regions (70, 72). The bottom region 72 can include a variety of virtual instruments including: additional user-defined waveforms, trendlines, an events log, measured minute averages and other options. The top region 70 includes real time airway flow and pressure waveforms (74, 76), which are displayed over different shades of gray to indicated the breath phase. The airway flow waveform 74 illustrates flow into the patient, or inspiration (positive flow), and flow out of the patient, or exhalation (negative flow). The pressure waveform 76 illustrates that the patient's airway rises above ambient for inspiration and falls during exhalation. The waveforms are tracked by a cursor that can be programmed to follow a peak, average, plateau or manually set position. The waveforms are displayed in fixed axis, moving erase bar format. The time axis resolution is user adjustable and displays time in seconds. Overwriting of the display starts at the beginning of an inspiration, so that the first displayed breath starts at a fixed point on the screen. The vertical axes are scaled to keep the displayed waveforms and settings in clear view.

The right side 77 of the display screen normally includes a flow-volume loop 78, a pressure-volume loop 80 and a minute volume wheel 82. A control slider and other optional panels can overlay this side when a user so desires. The flow-volume loop 78 is updated each breath to show the timing of delivered airflow. The vertical axis of the loop shares a common range and alignment with the airway flow waveform 74. The pressure volume loop is updated each breath to show the condition of the lungs. The vertical axis of the loop shares a common range and alignment with the pressure waveform 76. Calculated resistance and compliance are also displayed.

The minute volume wheel 82 provides a comprehensive summary of the patient's breathing for the last minute. The minute volume wheel displays a wealth of historical breath information (e.g., minute volume, inspiration phase, exhalation phase, inspiration/exhalation ratio, breathing rate, spontaneous minute volume, inhale tidal volume, exhale tidal volume, leakage) on a single integrated graphic circle so that the clinician can readily evaluate ventilation during the last minute.

Referring to FIG. 8, a minute volume wheel 84 represents one minute of ventilation as a circle with an area corresponding to measured minute volume. The measured minute volume is represented numerically, as the center number, and graphically, as a circle 86 drawn over a background circle 88 that has an area corresponding to the target minute volume. When the measured minute volume is exactly equal to the target minute volume, the two circles are blended in color and appear as one circle. When the measured volume is larger than the target volume, the background circle bleeds through and is visible. When the measured volume is smaller than the target volume, an uncovered portion of the background circle is visible.

One minute of ventilation is drawn as a circle 90, one wedge at a time, and is redrawn once a minute. Like the face of a watch, each degree of the circle 90 corresponds to one sixth of a second. Each inspiration is drawn as a wedge 92 with an area corresponding to delivered volume. This wedge is drawn over an inspiration spoke 94 that extends to maximum minute volume. Each exhalation is drawn as a wedge 96 with an area corresponding to exhaled volume. This wedge is drawn over an exhalation spoke 98 that extends to maximum minute volume. The spokes indicate breathing regularity and inhale to exhale (I:E) time ratio, and the wedges indicate tidal volumes. Difference between the radius of inspiration and exhalation wedges indicates the I:E ratios. The I:E ratio and breathing rate are also represented numerically (100, 102). The pairs of inspiration and exhalation wedges are coded by color to indicate spontaneous breaths, those triggered and partially controlled by the patient, and mandatory breaths, those triggered and controlled by the ventilator. The ratio of the colored areas indicates the ratio of spontaneous to mandatory breathing during the minute just past.

Referring, again to FIG. 7, the display controller provides a method for clinician control of the displayed waveforms. Each waveform (74, 76) is continuously measured and displayed on a background that changes color to indicate the phase of a breath. The rectangular area 200 for any phase of the waveform (74, 76) is used as a target for the touchscreen. When the clinician selects a phase of a waveform, the display controller displays the associated ventilator controls for available for adjustment by the clinician.

The display controller provides cursors 201 which are actually floating windows. More specifically, windows of one or two pixels width float over the waveforms (74, 76), thereby creating cursors 201. Since the cursors are independent of the background waveform graphics, numerous advantages result including drawing optimization, dynamic repositioning based on changing waveform values, positioning based on user interface gestures.

The background of the waveform (74, 76) includes color shading to indicate breath phase, title, units and scale information. Redrawing these graphics as new waveform samples are displayed generally requires substantial computer time, and the display controller performs this function efficiently notwithstanding the complexity of the background image. To perform this task efficiently, background images are created once. A narrow rectangular region 202 is removed from these images and pasted in front of the moving waveform to clear out the previous waveform and refresh the background prior to the new waveform. The width of the rectangular area 202 is kept sufficiently small so that the refresh is smooth in appearance. The x-axis coordinate of the current waveform position is used to control the x-axis position from which to remove a strip of background image. Multiple color coded background images can be maintained (e.g., three gray shades for the breath phases) and images removed from the desired one depending on the state of the waveform.

By selecting one of the control buttons on the touch display, the clinician 16 can display the control slider 106 for the control setting in a fixed location at the right of the screen, as shown in FIG. 9. A scroll bar title 108, located near the top of the slider 106, indicates the name of the control setting. The full vertical range 108 indicates the allowed set limits. The center slider indicates the current position 110 and the range 112 of the control setting. The upper and lower sliders (114, 116) indicate the current alarm limit settings. The position 110 of the current setting within the allowable range 112 and within the alarm limits (114, 116) is readily apparent to the clinician. The clinician can move any of the sliders to change the set values in steps of approximately 1% of the allowable range, or with the "Exact" button selected, approximately ten times more precision (i.e., about 0.1% of the allowable range). When the desired value is reached, the clinician depresses the Accept Changes button to change the parameter.

Alarm settings are matched with control settings in the appropriate control sliders. Some control settings have two associated alarms, others have only one associated alarm or do not have any associated alarms. For example, both high and low inspiratory pressure alarms are provided on the Airway Pressure control slider. If an alarm limit is exceeded during operation, the alarm is displayed in an alarm window, and an audio alarm turns on. Alarms are non-latching, i.e., the alarm indication turns off when the detected level no longer violates the set limit. Available control settings and ranges, alarm settings and ranges, and measured parameters are listed in the following table:

| Control Settings | |
| --- | --- |
| Tidal Volume (Compliance Compensated) | 50 to 2000 mL |
| Breathing Rate | 2 to 150 bpm |
| Peak Inspiratory Flow (BTPS Compensated) | 10 to 120 L/min |
| Oxygen Percentage | 21 to 100% |
| Peak Inspiratory Pressure | 2 to 120 cmH$_2$0 |
| Exhalation Assist | 0 to 30 cmH$_2$0/L/sec |
| PEEP | 0 to 20 cmH$_2$0 |
| Inspiratory Time | 0.2 to 4 sec |
| Inspiratory Pause Time | 0 to 1 sec |
| Sensitivity (Patient Effort Trigger) | 0 to 250 mL |
| Flow Drop-Off Percentage (Percent of Peak) | 5% to 80% |
| Humidifier Temperature | 30 to 60° C. |
| Airway Temperature | 15 to 40° C. |
| Waveform Shape (clinician modifiable) | custom, square decelerating, modified fine |
| Monitored and Displayed Parameters | |
| Exhaled Tidal Volume (Compliance Compensated) | 50 to 2500 mL |
| Measured Breathing Rate | 2 to 150 bpm |
| Peak Inspiratory Flow (BTPS Compensated) | 10 to 120 L/min |
| Oxygen Percentage | 21 to 100% |
| Peak Inspiratory Pressure | 0 to 120 cmH$_2$0 |
| PEEP | 0 to 20 cmH$_2$0 |
| Mean Airway Pressure | 0 to 120 cmH$_2$0 |
| Inspiratory Time | 0.1 to 4 sec |
| Inspiratory:Expiratory Ratio | 0.1 to 10.0 |
| Minute Ventilation - Controlled | 0 to 99 L/min |
| Minute Ventilation - Spontaneous | 0 to 99 L/min |
| Airway Temperature | 15 to 40° C. |
| Lung Compliance | 10 to 150 mL/cmH$_2$0 |
| Airway Resistance | 1 to 60 cmH$_2$0/L/s |
| Leak | 0 to 20 L/min |
| Airway Flow Waveform | −120 to +120 L/min |

| -continued | |
|---|---|
| Airway Pressure Waveform | −20 to +60 cmH$_2$0 |
| Flow-Volume Graph, Pressure Volume Graph | see text |
| Fresh Gas Flow Bar Graph | see text |
| Minute Volume Wheel | see text |
| Alarms and Indicators | |
| High/Low Exhaled Tidal Volume Alarm | 50 to 2000 mL |
| High/Low Respiratory Rate Alarm | 2 to 150 bpm |
| Low Oxygen Fresh Gas Flow | Automatic, % O$_2$ dependent |
| Low Air Fresh Gas Flow | Automatic, % O$_2$ dependent |
| Low Oxygen Supply Pressure Alarm | 25 psig |
| High/Low Airway Pressure Alarm | 2 to 120 cmH$_2$0 |
| High/Low Inspiratory Time Alarm | 0.2 to 4 |
| High/Low Inspiratory:Expiratory Ratio Alarm | 0.1 to 4.0 |
| High/Low Minute Volume Alarm | 1 to 40 L/min |
| Airway Leak Alarm | 1 to 20 L/min |
| Patient Disconnect Alarm | Automatic |
| Apnea Alarm/Backup Ventilation | 30 |
| Internal Battery Notification Alarm | Battery in Use % Remaining |
| Pneumatic System Fault Alarm | Automatic |
| Alarms Silence | 120 |
| High/Low Oxygen Alarm | 18-100% O$_2$ |

In one embodiment, the display screen 24 is covered by a resistive touchscreen. Known touchscreen interfaces require that the user touch a graphic object on the screen, but this action generally obscures the object. The touchscreen interface of the present invention defines an area whose shape, size and position is dynamically computed based on the characteristics of the associated graphic object. The interface interprets touching by the user as a manipulation of the associated graphic object. More specifically, a dragging motion moves the associated object, or change its value or other attributes.

Referring again to FIG. 9, the display controller includes software for manipulating the characteristics of the breath parameter Airway Pressure 106 displayed in the control slider 104 on the touch-sensitive display 24. When the clinician 16 selects a control button to display the control slider 106 for Airway Pressure, the display controller 12 dynamically defines a touch zone on the touch-sensitive display. More specifically, touch zones are defined for each slider (i.e., high alarm, low alarm, position and allowable range) within the control slider. Each touch zone is slightly larger than the displayed slider. By way of example only, the touch zone for high alarm may extend into regions 118 to either side of the color coded high alarm region 114. The display controller 12 receives a touch signal when the clinician 16 touches any location within the touch zone and changes the range of the high alarm slider breath parameter in response to the touch signal. In other words, the display controller 12 increases the high alarm limit in response to the clinician 16 touching a location within the region 118 and dragging his finger in a upward path. Because his finger does not obscure the high alarm limit, the clinician can actually see the limit being changed as it happens.

Referring also to FIG. 10, the display controller 12 includes software for providing precise numerical control without the requirement of a keyboard. The display controller 12 displays a window 120 that looks like a numeric text field, but has a background color to distinguish the left region 122 from the right region 124, relative to the decimal point. Once either numeric region 122, 124 has been touched, a larger touch sensitive area 126, 128 respectively is associated with each of the numeric regions. When the clinician 16 touches a touch sensitive area and moves in a vertical path, the interface provides continuous numeric feedback by increasing or decreasing the displayed value.

3. Embedded Controller—Referring again to FIG. 1, the embedded controller electronics 14 is based around microprocessors 31, 32. The microprocessor 32 is in electrical communication with the ventilatory unit 17 and the microprocessor 31 is in electrical communication with the sensor monitoring system 19. The embedded controller relies on industry standard bus based modules to perform certain functions and custom printed circuit boards to perform other functions. The modules, the printed circuit boards, the ventilatory unit pressure processors 32 and the airway processor 31 are mounted on or connected to on a main printed circuit board 28. A real time operating system is the foundation of the embedded controller software, which runs the algorithms required for measurement and control. A power system converts line power and provides battery backup for a average of one hour. The embedded controller 14 has microprocessor and associated input/output hardware to provide for closed loop control of pneumatic system 41 and the acquisition of patient data. The embedded controller 14 communicates the status of the patient and its own status to the display controller 12. The embedded controller 14 responds to commands and setting changes received from the display controller 12, and maintains a non-volatile record of instrument settings to maintain operation in the absence of both communication from the display controller and line power.

The embedded controller 14 performs real time data acquisition of twenty three different analog input signals including:

| | | |
|---|---|---|
| 1. | Flow | Oxygen, |
| 2. | Flow | Air, |
| 3. | Flow | Third Gas, |
| 4. | Flow | Canister, |
| 5. | Flow | Exhaust, |
| 6. | Pressure | Patient Airway, |
| 7. | Pressure | Canister, |
| 8. | Flow | Low Exhaust, |
| 9. | Temperature | Airway, |
| 10. | Temperature | Humidifier, |
| 11. | Voltage | Battery, |
| 12. | Current | 5 Volts, |
| 13. | CO$_2$ | Airway, |
| 14. | Voltage | ECG, |
| 15. | Voltage | QRS, |
| 16. | Temperature | Patient Temperature 2, |
| 17. | Pressure | Patient Pressure 1, |
| 18. | Pressure | Patient Pressure 2, |
| 19. | Signal | PT34, |
| 20. | Voltage | Aux 1, |
| 21. | Voltage | Aux 2, |
| 22. | Voltage | Aux 3, |
| 23. | Voltage | Aux 4. |

The embedded controller 14 also monitors six switches:

| | | |
|---|---|---|
| 1. | Pressure | Oxygen, |
| 2. | Pressure | Air, |
| 3. | Pressure | Third Gas, |
| 4. | Pressure | Safety Valve, |
| 5. | Voltage | Power Switch, |
| 6. | Voltage | No AC Line. |

The embedded controller controls nine digital outputs:

| | |
|---|---|
| 1. Solenoid | Exhaust Flow Zero, |
| 2. Solenoid | Canister Flow Zero, |
| 3. Solenoid | Safety Valve, |
| 4. Solenoid | Direction (I/E), |
| 5. Heater | Canister, |
| 6. Heater | Fresh Gas Tube and Humidifier, |
| 7. Power | CRT Display, |
| 8. Alarm | Beeper, |
| 9. Battery | Backup. |

The embedded controller 14 controls four duty cycle modulated digital outputs:

| | |
|---|---|
| 1. Flow valve | Canister, |
| 2. Flow valve | Air, |
| 3. Flow valve | Oxygen, |
| 4. Flow valve | Third Gas. |

The embedded controller 14 communicates with the display controller 12 via a shared memory interface 15 at a data transmission rate exceeding 100K bytes per second.

4. Data Structures—This section describes the architecture for software utilized in the embedded controller and shared with the display controller. The architecture of the software is built around the concepts of therapy controls, mode controls, breath controls, phase controls and cycle controls. A data structure driven state machine determines the control parameters for each therapy control, mode control, breath control, phase control, cycle control and exhalation assist.

Referring to FIGS. 1 and 11, the figures illustrate the data structure hierarchy for the ventilator control system. Using an input device 26 such as the touch-sensitive display 24 within the display controller 12, a clinician can change ventilation control settings to create a new therapy comprising a therapy control structure 140. The settings are validated by the display controller 12, placed into a new therapy control structure and sent to the embedded controller 14. The embedded controller 14 validates the settings again and checks the integrity of the new structure before the new therapy control is accepted. Also, the clinician 16 may simulate the behavior of the new therapy control using a simulator and may allow others to utilize the therapy control by adding it to the database 13. In any case, the clinician 16 sends the new therapy control structure to the memory for use by the embedded controller 14 in controlling the pneumatic system 41. A therapy control structure 142 (or a mode control) 140 is defined as a collection of mode control structures 142 and mode switching rules 144. A mode control structure (or a breath control) is defined as a collection of breath control structures 146 and breath switching rules 148. A breath control structure 146 (or a phase control) is defined as a collection of phase control structures 150 and phase switching rules 152. A phase control structure 150 (or a cycle control) is defined as a collection of ventilator control settings 154 and an array of waveform samples 156. Phase definitions and requirements for transitions between phases are tied directly to measurable system performance, and correlate closely to published descriptions of the desired behavior of mechanical ventilators.

More specifically, the therapy control structure 140 is a nested hierarchy of increasingly complex control structures. A cycle (e.g., a 4 msec time slice) occurs within cycle control, which occurs within phase control, which occurs within breath control, which occurs within mode control, which occurs within therapy control, which is the clinically specified therapy that drives the ventilator pneumatic system 41. Once each cycle, ventilation control moves from one control state to another control state.

After each cycle, when the hierarchy of rules is tested and the state is set for the next cycle, a new therapy control structure 140 may cause a branch to the first cycle of the first phase of the first breath of the first mode of ventilation within the new therapy control structure, or the new therapy control structure may be delayed a few cycles until better patient synchrony can be achieved. Within a therapy, there is a collection of mode control structures 142 and a collection of rules specifying how and when to switch from one mode of ventilation to another one. Thus, a therapy may define several different modes of ventilation and mode switching rules 144 for the transition from one mode of ventilation to another.

After each cycle, when the hierarchy of rules is tested and the state is set for the next cycle, the mode switching rules 144 may cause a branch to the first cycle of the first phase of the first breath of another mode of ventilation within the therapy control structure 140. Within a mode, which is within a therapy, there is a collection of breath control structures 146 and a collection of breath switching rules 148 specifying how and when to switch from one breath type to another breath type within the same mode. Thus, a mode of ventilation may have several different types of breaths defined, and rules specified for how to go from one breath type to another.

After each cycle, when the hierarchy of rules is tested and the state is set for the next cycle, the breath switching rules 148 may cause a branch to the first cycle of the first phase of another type of breath within the mode. Within a breath, within a mode, within a therapy there is a collection of phase control structures 150 and a collection of phase switching rules 152 specifying how and when to switch from one breath phase to another phase within the same breath. Thus, a breath type may have several different phases defined, and rules specified for how to go from one breath phase to another. For example, breathing generally proceeds from an inspiration phase to a pause phase to an exhalation assist phase to a PEEP phase, but these phases may be further subdivided for a finer granularity of control.

After each cycle, when the hierarchy of rules is tested and the state is set for the next cycle, the phase switching rules 152 may cause a branch to the first cycle of the next phase within the breath type. Within a phase, within a breath, within a mode, within a therapy, there is a ventilator control setting structure 154. This structure contains an array of samples that comprise a specified waveform shape. During each cycle, the control logic is driven by the waveform sample specific for the cycle, and by a collection of ventilator control settings 154 specific for the phase. The cycle time is in milliseconds, and is currently set to four milliseconds.

After performing all ventilation control for the cycle, the hierarchy of rules is tested and the state is set for the next cycle, which is by default the next cycle within the current phase, current breath type, current mode of ventilation and current therapy. However, higher level rules may cause a change in breath phase, breath type, mode of ventilation, or an entirely new therapy may be specified by the clinician and take control at the next cycle.

Each ventilator control setting structure 158 contains necessary and sufficient information to control one parameter of ventilation, including whether there is a high alarm level, whether the high alarm is active, whether there is a control level, whether the control is active, whether there is a low alarm level, whether the low alarm is active, whether there is a range level, whether the range is active, and a range target control structure to define how and why the parameter is to be adjusted automatically within the specified range. Each phase control structure has its own collection of ventilator control settings, although in practice, phases within a breath generally share the same collection.

The data structure-driven architecture described above enhances safety and reduces the likelihood of hazardous conditions by permitting non-programmers to review and understand the function of the ventilator control system.

Several breath control structures are predefined in the embedded controller. These breath control structures are used when hazards are detected, such as apnea or patient circuit disconnect. They are also used to support the patient if the communication link between the display controller 12 and embedded controller 14 is lost. Also, the embedded controller 14 checks the integrity of every therapy control structure sent by the display controller 12. If a requested change is invalid, the embedded controller 14 continues operation with the last known valid therapy control structure. If no valid therapy control structure has been received, the embedded controller 14 uses the predefined breath control structures to continue patient support.

FIG. 12 is a flowchart of an embodiment of an algorithm executed by the exhalation assist device embodied in FIG. 1. The algorithm begins with the clinician 16 entering the desired values relating to airway resistance or negative pressure in the ventilatory unit (Step 1). These values are then compared with data relating to airway resistance or negative pressure in the ventilatory unit that have been measured or calculated by the data processing unit (Step 2). It is then determined whether these sets of data are equal to each other or are within a predetermined range of each other (Step 3). If these values are equal or within a predetermined range, airway flow is then measured (Step 5). If these values are not equal or within a predetermined range, the applied negative pressure is adjusted (Step 4), and then the airway flow is measured (Step 5). After airway flow is measured, it is determined whether the measured airway flow is a positive or a negative number (Step 6). If airway flow is positive, indicating that inspiration is occurring, a new measurement of airway flow is obtained (Step 5). If airway flow is negative, indicating that exhalation is occurring, airway pressure is measured (Step 7). It is then determined whether airway pressure is greater than zero and less than PEEP (Step 8). If airway pressure is greater than zero and less than PEEP, airway resistance is calculated and pressure in the ventilatory unit is measured (Step 9). After these measurements and calculations are made, the cycle recommences (Step 2). If airway pressure is not greater than zero and less than PEEP, it is determined whether the alarm has been overridden (Step 10). If the alarm has been overridden, airway flow is measured on the next breath (Step 5). If the alarm has not been overridden, the alarm is triggered (Step 11). If the alarm is triggered, the cycle must be restarted with the input of desired values (Step 1).

5. Simulator—Referring again to FIG. 1., a simulator 212 is provided for predicting the status of the pulmonary system of a patient and a database 13 for storing actual or simulated historical patient protocols. The simulator 212 is electrically connected to the display and embedded controllers 12, 14 respectively. The simulator 212 uses a set of breath parameters provided by the clinician 16 via the input device 26 to predict the status of the patient's pulmonary system. The simulator 212 simulates the adjustment to the ventilator pneumatic system 41 in response to the set of breath parameters and the response of the patient's pulmonary system to the adjusted pneumatic system 41. The predicted status and the set of breath parameters are displayed on the display screen 24 (FIG. 13).

An advantage of the simulator 212 is that the clinician 16 can experiment with new or old settings, while the actual settings remain unchanged and the patient is unaffected. When the clinician 16 begins changing settings in the simulation mode, the ventilator control system 10 predicts the effects of the change and displays the predicted result on the display 24. The simulator 212 uses a standard two parameter model of a respiratory system and the current calculated values of the patient's resistance and compliance to predict the effect. The model assumes no contribution from the patient's respiratory muscles (i.e., a passive inspiration and exhalation cycle). The model used is:

$$\text{Airway Pressure} = (\text{Delivered Volume}/\text{Lung Compliance}) + (\text{Airway Flow} \times \text{Airway Resistance}).$$

A change in patient intervention in current ventilators typically requires multiple setting changes. Implementing such setting changes is greatly complicated by the series of indeterminate control states as one setting is changed at a time. Using the simulator 212, the clinician 16 can change multiple settings until the predicted waveforms are satisfactory and then activate all the changes simultaneously. If the clinician 16 is dissatisfied, he can quickly and conveniently return the control settings to their previous values without adversely affecting the patient.

The clinician 16 can also use the simulator 212 to select a mode of ventilation or sequence by modes, by choosing a programmed comprehensive therapy control structure. Those breath parameters, which are essential to the definition of the mode, are highlighted with a color-coded background. Other controls are listed as active or inactive. The explicit list of active controls clearly delineates the exact function of the mode and alleviates confusion caused by inconsistent or incomplete definitions. Moreover, the simulator 212 can precisely replicate the behavior of modes on preexisting ventilators. The clinician 16 can make adjustments to the list of controls to accurately simulate the ventilator that a hospital's staff has been trained to use. The list of controls together with the simulated behavior can help teach the effects of various modes on patients, rather than the ventilator-specific mode definition.

As claimed in FIG. 13, while the simulator 212 predicts the shape of the breaths using the two parameter model, and displays the simulation on the display 24, many other physiological models and predictions may be possible. Specifically, the simulator 212 may predict the effect of positive end expiratory pressure on lung volume and functional residual capacity; it may predict the effect of minute volume on blood oxygen and carbon dioxide levels; it may predict the effect of mean airway pressure on pulmonary blood flow; and it may provide other similar models.

Referring also to FIG. 1, the database 13 assists the clinician 16 in managing the intervention and in tracking patient status. The database 13 makes large amounts of stored patient data available at several levels of detail and encourages comparison of different patient data. The clinician 16 can compare stored historical patient data with current settings to learn whether the current intervention has been effective and whether the patient is progressing.

The database 13 is electrically coupled to the display controller processor 22 and stores a plurality of patient protocols. Each patient protocol includes at least a set of breath parameters and patient data. The breath parameter may be organized as one or more therapy control structures. The clinician 16 selects a patient protocol by depressing a touch zone on the display 24. The processor 22 copies the selected patient protocol into memory. In the operational mode, the processor 22 instructs the embedded controller 14 to simultaneously adjust the controls of the pneumatic system 18 using the selected patient protocol. In the simulation mode, the simulator 212 simulates the adjustment to the ventilator pneumatic system 41 and the resulting response of the patient's pulmonary system.

The processor 22 stores patient protocols as epochs, which are complete "snapshots" of a particular time or event. The processor 22 uses real time event and pattern discrimination to determine when to store epochs of interest. In this way, the clinician 16 does not have to decide a priori what may be important, what to "trend", or how to process the data. Because all the data is stored, it can be post processed to reveal any aspect of the patient's previous condition. The saved epochs are organized in the database. Access to the epochs can be by time, by event, or by area of interest. The ability to overlay data from previous epochs informs the clinician as to whether the patient is progressing, or whether the intervention is working as expected.

FIG. 14 is a detailed functional block diagram of the simulator feature of the ventilator control system 210. The clinician manipulates a control setting slider 216 to change or set a ventilator control setting. The clinician's input are stored in a memory 218. The simulator 220 receives the inputs and creates a phase control structure, a breath control structure, a mode control structure, or a therapy control structure for use in its simulation. If, for example, the clinician 16 decides to use the breath control structure 222 to change the patient's therapy, the selected breath control structure (which is embedded within a mode control structure within a therapy control structure) is transmitted to the embedded controller (at 224) via the shared memory interface. The embedded controller validates the settings within the breath control structure 226. The processor implements the validated therapy control structure 228, which includes the breath control structure, in a breath control algorithm 230 and provides signals 232 to the pneumatic system for simultaneously changing one or more control settings.

7. Waveform Shaper—The waveform shaper shown in FIG. 15 is a graphical tool which enables a clinician to shape one or more phases of a breath. Characteristics such as the rise time and shape 130, the plateau length and shape 132, the fall time and shape 134 can be drawn to any desired characteristics by the clinician. In one embodiment, the phases can be shaped by touching the various active areas dynamically created on the touchscreen display displaying the waveform shaper and drawing the finger in the desired direction. In another embodiment, control buttons may be selected to add characteristics to the waveform, specifically sinusoidal or pulse-like variations about an average level during a phase. The waveform shaper is displayed by the display controller 12, wherein its output is used to fill the array of waveform samples 156 in the cycle control structure of the therapy control structure 140. The pneumatic system 41 in communication with the embedded controller 14 can in this way be directed to follow any arbitrary waveform "drawn" by the clinician for one or more phases of a breath.

8. Interface Protocol—The patient data waveforms are driven by a data stream protocol. The data stream can be generated by sensors, which is the usual manner in which the ventilator operates, by the simulator 212 which uses the breath parameters and measured patient parameters to generate simulated sensor data, or by the stored sensor data in epochs to show historical patient behavior. The ability to use the same interface to display real data, simulated data and epoch data is an important feature of the ventilator control system.

9. Integrated Control/Data/Alarm Display—Referring again to FIG. 7, patient data waveforms 74,76 presented on display screen 64 of the display controller 12 combine setting control, data and alarm displays in a single region. The association of numbers and graphic icons with the data waveforms provide context to illuminate the meaning of the numbers and icons without unnecessary data or unit labels. A light line 201 is apparent as peak flow or pressure; a heavy bar 204 is apparent as the peak pressure set level; a light bar 203 is apparent as a high pressure alarm setting; an active rectangular region 200 on the pressure waveform is apparent for setting the exhalation pressure level. Differences between desired and actual settings, and alarm margins are readily apparent. The simplicity of these representations can be contrasted to a typical list of controls, calculated data, and alarms, where each item on the list is in LABEL:VALUE:UNITS format and the integration and comparisons must be performed in the head of the clinician.

10. Therapy Programming—Referring also to FIG. 16 is an illustration of a therapy programming screen 205 provided by the display controller 12. With this screen, the clinician 16 can create or modify one or many breath parameters to prescribe a new type of therapy for the patient. Changes made are reflected at one or more data structure levels in the therapy control structure created in the display controller 12. After validation, the new therapy control structure can be sent to the embedded controller 14 for immediate implementation, or saved to a list of therapy prescriptions for later use.

A therapy can thus be built from the simple to the complex. Breath parameters are selected and changed to modify and combine cycles to define a phase; to modify and combine phases to define a breath; to modify and combine breaths to define a mode; and to modify and combine modes to define a therapy program. The selections are reflected in the hierarchy of structures in the therapy control structure, as previously described. The collection of settings are given a title by the clinician, in common use loosely defined as a mode of ventilation. The creation process, with its explicit connection of breath parameters to a mode definition, helps clarify the way the therapy will affect the patient.

In one embodiment, the therapy programming screen 205 enables selection and changing of related breath parameters. The therapy prescription to be altered is selected from a list; a new therapy prescription can be created by selecting a similar prescription from the list, giving it a new title, and altering it as needed. A mode within the selected therapy prescription is selected; a breath within the selected mode is selected; a breath parameter control setting within the selected breath is selected; a sequence which identifies a specific, hierarchically nested breath parameter. Features of the breath parameter are toggled on or off, or chosen from lists which are brought forth when there are more than two choices. Every breath parameter, within each breath, within each mode, must be programmed to complete the therapy prescription.

Referring to FIG. 16, a control definition section 207 is displayed adjacent to the control slider previously described. The control definition section 207 includes a title 209 of the therapy prescription. The title in this example includes two modes, and the mode (A/C pc) to which the selected breath parameter is tied is highlighted. The control setting for the breath parameter may have a range feature enabled 211, which, if enabled, will bring forth a panel of selected targets appropriate for the range, and which, if enabled, means that the ventilator control system will seek to accomplish a range target goal 213 by varying the control setting within the range specified in the control slider. The control setting may be required to be on 215, meaning that it cannot be turned off by the clinician when operating within this breath type within this mode. It may be required to be off 17, meaning that it cannot be turned on by the clinician when operating within this breath type within this mode.

The therapy programming screen allows the control setting to be shared by one or more other breath types 219 within the mode, or within the paired modes, such that any adjustments to the control setting will affect all such breaths. It allows control settings to be highlighted 221 as having primary importance to clinicians making adjustments to therapy. It allows multiple breath types to be defined, and provides a selection of rules that will be tested to determine which breath type to use within the mode.

The embodiment allows the clinician to select from a number of triggers which determine the transition between modes of ventilation 223, when a multi-mode feature is enabled 225. The triggers for transition may be different depending on the direction of the transition. For the example shown, the trigger for the transition from variable pressure support (VPS) to assist control (A/C pc) is minute volume (MV), while the trigger for the transition from assist control to variable pressure support is sensitivity (Sense, i.e. patient effort).

While the particular embodiment permits the programming of two modes, due to conceptual limitations for this new capability on the part of clinicians, another embodiment includes therapy prescriptions which encompass many modes, with multiple triggers for the transitions between modes. Specifically, other prescriptions include sequences of modes which automatically change the treatment of a patient as his condition changes, and allow the clinician to readily control the sequence. Other prescriptions permit time limited modes, which turn on for a period and then revert to the mode, or combinations of modes, in effect prior to their turn on. The therapy programming screen enables the clinician to tune the therapy to the specific and ever changing needs of the patient, with much more power and flexibility than selecting from a set of simple ventilator modes preset by the manufacturer.

11. In another aspect, the ventilator, according to the invention, operates using several mode control structures in a paired configuration, which includes a primary mode control structure and a secondary mode control structure. Such paired mode control structures include Pressure Support-Variable Pressure Control (PS-VPC), Variable Pressure Support-Variable Pressure Control (VPS-VPC), and Continuous Positive Airway Pressure-Assist Control/Pressure Control (CPAP-A/C/pc). The primary mode control structure provides support to a spontaneously breathing patient. The secondary mode control structure is a mode control structure in which the ventilator provides full support to the patient with mandatory breaths. The mode transition trigger for switching between the primary and secondary mode control structures is a patient Minute Volume Trigger (MVT). In one embodiment, the clinician sets a minute volume threshold, which allows the patient and respiratory patterns to control whether the primary or secondary mode control structure is still active. If the patient exerts enough effort to drive the minute volume above the MVT level, the primary (spontaneous) mode control structure will become active. If spontaneous patient effort is not sufficient to exceed the MVT level, or if there is no spontaneous effort, the second mode control structure will remain active.

In one embodiment of this aspect of the invention, Automatic Pressure Support (APS) mode is a primary mode control structure paired with VPC, a secondary control mode structure. APS automates weaning of the patient from a ventilator and protects against patient respiratory failure indicated by the patient's increasing respiratory rate.

In a typical clinical setting, progressive withdrawal, i.e., weaning of a patient during pressure support ventilation requires that a clinician titrate the pressure level until a desired patient stable breathing pattern is achieved. The patient's tolerance to this pressure support level is subsequently monitored and after a specified time interval, the clinician manually decreases pressure support, typically by 2-4 cm $H_2O$. If the patient exhibits rapid shallow breathing, the pressure is manually increased by the clinician to a previous level. This requires many interventions by the clinician.

In the APS mode, APS is used in a paired mode configuration in conjunction with VPC to obviate the necessity of frequent clinician interventions and prolonged clinician involvement with the ventilator weaning process. This automates the weaning of a patient from a ventilator. In VPC, the operating pressure range for ventilating a patient is set. The ventilator continuously adjusts the pressure in order to provide a minimum pressure required to deliver a set tidal volume. A breathing rate is set and the ventilator delivers mandatory breaths to maintain the minimum breathing rate. The patient may initiate breaths above the set breath rate by exerting a minimum effort, as set by the clinician, and the ventilator will provide the pressure support required to deliver the set tidal volume. The set tidal volume may be exceeded if the patient exerts enough effort.

In the APS-VPC dual mode, as in other dual modes, the mode transition trigger for switching between the primary and secondary mode control structure is patient minute volume. The MVT level is predetermined and set by the clinician. When the patient's minute volume is below the set MVT level, the ventilator remains in VPC. When the patient exerts enough effort to drive the minute volume above the set MVT, the APS mode will become active In the event that the patient stops breathing spontaneously, at least one of two events occur. Either the minute volume falls below the trigger level, or the apnea alarm is triggered because the breathing rate is below the lower alarm limit. If either or both occur, the ventilator is triggered back into VPC mode.

In the APS-VPC embodiment for weaning a patient from a ventilator described herein, the initial pressure support level is determined by assigning the current VPC pressure support level of the patient and ventilator in the VPC mode, as the initial pressure support level for APS. This ensures a smooth transition for the patient and removes the guesswork and the lengthy process of determining the pressure support level by the clinician to begin weaning of the patient from the ventilator. In the APS-VPC mode, the patient's effort in VPC mode determines the initial pressure support level.

After the patient has made the transition from VPC into APS, the pressure support level is automatically decreased at a constant preset rate. As the pressure support level is decreased, the patient is challenged to initiate a spontaneous breath. A Rate Range of breaths per minute is set by the clinician. As long as the patient's spontaneous breath rate remains within the Rate Range, pressure support will automatically decrease at a constant rate. In one embodiment, the spontaneous breath rate is measured frequently as on a breath-by-breath basis. The clinician sets a Low Pressure Alarm Level below which the pressure support level can not be reduced. The effect is to automate the weaning process with an automatic withdrawal of mechanical ventilation using a closed loop control for pressure support.

Another feature of the APS-VPC mode includes detection and mitigation of shallow breathing. If the patient's spontaneous breathing rate exceeds the set Rate Range, pressure support will be increased. Once the spontaneous breathing rate returns to within the set Rate Range limit, the pressure support level starts to decrease. In addition, in the APS-VPC mode, increasing pressure support is avoided in patients with a high breathing rate and high tidal volume by monitoring the patient's Breathing Frequency/Tidal Volume (f/TV) ratio, described below.

In the APS-VPC mode, the MVT level must be reached for the ventilator to switch between the APS mode and the VPC mode. For example, if the patient' minute volume (MV) is below the MVT trigger, the ventilator remains in VPC, when the patient's MV is above the MVT level, the ventilator switches to APS mode when the patient breathes spontaneously.

In addition to monitoring and responding to the patient's minute tidal volume, the APS-VPC mode will revert to the VPC mode when the patient's spontaneous breathing rate falls below the lower limit of the set Rate Range. Once in the VPC mode, the patient is again supported until the patient initiates the weaning process. The cyclical nature of the automated weaning process allows the patient's effort to determine when the patient is ready to attempt a weaning trial and determines the duration of the weaning trial.

Referring to FIG. 17, in general, the process of automated weaning in the APS-VPC mode is as follows. The Tidal Volume Control and the Breathing Rate are set to the ON position. In Step 400 the clinician enters values for PS-INCR (described below), PS-DECR (described below), f/TV ratio limit (described below), Low Pressure Alarm Level, MVT, and Breath Rate Range. The patient begins breathing while the ventilator machine is in control mode VPC (Step 420). The starting pressure support (PS) level in VPC will be the initial pressure level. When a patient's spontaneous breath is detected (Step 430) and the patient's minute volume is greater than MVT (Step 440), the ventilator is switched from VPC mode to APS (Step 450).

The APS mode detects and mitigates shallow breathing during the automated weaning process. To detect and to mitigate rapid, shallow breathing, the patient's Breathing Rate and the frequency/Tidal Volume (f/TV) ratio are monitored.

After the patient has made the transition into the APS mode (Step 450), as the patient breathes, the pressure support level is automatically reduced by a constant percentage value of the pressure (PS-DECR) to challenge the patient to breath. The patient remains within the APS mode as long as two criteria are met: (1) the patient's minute volume must be greater than the set MVT level (Step 440), and (2) the patient's spontaneous breathing rate must be within the set Rate Range (Step 460). If these two criteria are met, the pressure support level is automatically reduced by a constant percentage value of the pressure (PS-DECR).

The PS-DECR is set during initial step 400 by the clinician on the ventilator control panel. The PS-DECR is a Rate % decrement ranging from 0.01% to 0.1%. In one embodiment, the clinician sets the Rate % decrement to 0.1. At this setting, for every spontaneous patient breath within the Rate Range set by the clinician, the pressure support level will be decreased one-tenth of a percent per patient breath on a breath-by-breath basis. In a particular embodiment, the Rate for PS-DECR is set at 0.01%. Increasing the rate % decrement will increase the rate at which pressure support is withdrawn from the patient. Reduction of the pressure support below a predetermined level is limited at the Low Pressure Alarm earlier set by the clinician in Step 400. Thus, the automatic weaning process is accomplished by automatic withdrawal of mechanical ventilation using a closed loop control for APS.

The patient's spontaneous breathing rate is monitored (Step 460) to determine if the breath rate is within the set Breath Rate Range. The patient's spontaneous breathing rate is measured as the lesser of (1) the Current Breath Rate, calculated by the interval between the last two breaths, and (2) the Average Breath Rate, a twenty breath average, and compared to the Rate Range (Step 470) set by the clinician on the Rate slider control. If the lesser of patients' spontaneous breathing rate as determined by (1) and (2), is less than the lower limit of the set Rate Range, the patient's f/TV ratio is compared (Step 480) to the f/TV ratio limit earlier set by the clinician in Step 400.

A frequency/Tidal Volume Ratio Limit (f/TV Ratio Limit) protects against automatic pressure support increase in a situation of patient high breathing rate accompanied by patient high tidal volume. The f/TV Ratio Limit is automatically calculated using the upper breath Rate Range value for the frequency and the Low Tidal Volume alarm limit set by the clinician. Both the f/TV Ratio Limit and the Low Tidal Volume alarm limit are determined and entered by the clinician at Step 400. The maximum allowable value for the f/TV Ratio Limit is 100. If the calculated f/TV Ratio Limit value exceeds 100, the f/TV Ratio Limit will default to 100. The f/TV Ratio Limit and the patient f/TV Ratio are displayed on the primary display screen.

If the lower of the two patient breathing rates (Average Breath Rate and Current Breath Rate) exceeds the Rate Range, and if the patient's f/TV Ratio exceeds the f/TV Ratio Limit, then the pressure support level is increased by PS-INCR (Step 490). PS-INCR is set during Step 400 on the control panel by the clinician. The PS-INCR is a Rate % increment ranging from 1% to 20%. In one embodiment, the clinician sets the Rate % increment to 5. At this setting, for every 5% increase in patient's Breathing Rate above the set Rate Range, the pressure support level is increased 1% for each patient breath. In a particular embodiment, the setting is 5%. Decreasing this control value will accelerate the rate at which the pressure level is raised for the patient. If the Average Breath Rate does not exceed the set Rate Range and the Current Breath Rate does, no adjustments are made to the pressure level. The effect is to gradually increase pressure support in order to cause a decrease in the patient's spontaneous breathing rate so that it falls within the Rate Range. When the f/TV ratio limit is no longer exceeded, pressure support starts to decrease.

The patient's spontaneous breath rate is monitored at step 500. If the spontaneous breath rate is less than the lower limit of the set Rate Range, the patient returns to VPC mode (step 420). If the patient's spontaneous breath rate is not less than the lower limit at the set Rate Range, patient is maintained in APS.

In the APS-VPC embodiment, alarm and control settings are matched in the appropriate control sliders. If an alarm limit is exceeded during operation, the alarm is displayed in an audio window and an audio alarm turns on. Additional channels, control settings, and ranges and alarm settings and ranges, and measured parameters are listed in the following table. All other controls and all standard safety alarms are the same as the standard pressure support mode.

| | |
|---|---|
| Patient f/TV Ratio Channel: breath rate/TV (L) on a breath-by-breath basis (displayed as a trend, waveform or digitally as a minute average) | 0-1000 bpm*/L |
| Average Patient f/TV Ratio Channel (average for the last 20 breaths) | 0-1000 bpm/L |
| Average Breath Rate Channel (average for the last 20 breaths) | 0-150 bpm |
| PS-INCR Control | 1-20% |
| PS-DECR Control | 0.01 to 0.1% |
| f/TV Ratio Limit | 20-110 bpm/L |
| P/Paw Variable Support Level determines high and low pressure and alarm limits as in PS | |
| Breath Rate determines when increased PS is required | On: range of values on slider |
| Default Settings | |
| Waveform Display | |
| Patient Frequency/Tidal Volume | 0-200 bpm*/L |
| Breathing Rate | 2-150 bpm |
| Pressure Support | 0-50 cm H$_2$O |
| Average Breath Rate | 0-40 bpm |
| Trend Display | |
| Minute Volume | 0-20 L/min. |
| Spontaneous Minute Volume Percent | 0-100% |
| Patient Frequency/Tidal Volume | 0-200 bpm/L |
| Breath Rate | 0-40 bpm |

*breaths per minute

What is claimed is:

1. A method for automatically weaning a patient from a ventilator, the method comprising the steps of:
   (a) providing pressure support to a patient;
   (b) detecting a spontaneous patient breath;
   (c) measuring the patient's spontaneous breathing rate;
   (d) measuring the patient's minute volume;
   (e) comparing the patient's spontaneous breathing rate to a predetermined range of breathing rates;
   (f) comparing the patient's minute volume to a predetermined tidal volume; and
   (g) modifying the patient's support level according to the patient's spontaneous breathing rate compared to the predetermined range of breathing rates, and the patient's minute volume compared to the predetermined minute volume.

2. The method for automatically weaning a patient from the ventilator of claim 1, the method further comprising the step of:
   (h) decreasing the patient's pressure support level if:
      (i) the patient's spontaneous breathing rate falls within the predetermined range of breathing rates, and,
      (ii) the patient's minute volume exceeds the predetermined minute volume.

3. The method for automatically weaning a patient from the ventilator of claim 1, the method further comprising the step of:
   (h) increasing the patient's support level if:
      (i) the patient's spontaneous breathing rate falls outside the predetermined range of breathing rate; and
      (ii) the patient's minute volume is exceeded by the predetermined minute volume.

4. The method of claim 1 further comprising adjusting the amount of pressure support between zero and PEEP.

5. The method of claim 1 wherein the patient's pressure support level is decreased by a rate between 0.01% and 0.1%.

6. The method of claim 1 further comprising setting a low pressure alarm limit.

7. The method of claim 1 wherein measuring the patient's spontaneous breath rate further comprises calculating an average breath rate and a current breath rate from patient's spontaneous breath rate to obtain the patient's breath rate.

8. A ventilator system for automatically weaning a patient from a ventilator, comprising:
   a source of pressure in communication with the patient to provide pressure support to the patient;
   a spontaneous breathing rate monitor;
   an input device for receiving input values for a predetermined breath rate range and a predetermined minute tidal volume;
   a minute volume flow meter; and
   a data processing unit in electrical communication with said pressure source, said breathing rate monitor, said flow meter, and said input device, wherein, said data processing unit calculates an average breath rate and a current breath rate from a signal from said breathing rate monitor to obtain the patient's breath rate, compares the patient's breath rate to the predetermined breath rate range, compares the patient's minute tidal volume to the predetermined minute tidal volume, and adjusts the pressure source to change pressure support in response thereto.

9. The ventilator system of claim 8 wherein said source of pressure comprises a pneumatic system comprising a flexible airway, a source of pressurized gas, a rigid chamber, a flexible chamber and a Venturi valve.

10. The ventilator system of claim 9 further comprising a high speed pneumatically driven, electronically controlled proportional valve and dual Venturi systems.

11. The method of claim 10 further comprising calculating an average breath rate and a current breath rate to obtain the patient's breath rate.

12. The ventilator system of claim 8 wherein said input device is a touch screen in electrical communication with a display controller processor.

13. The ventilator system of claim 8 wherein said data processing unit is a real time data processor in electrical communication with a ventilatory unit processor and an airway processor.

14. A method for automatically weaning a patient from a ventilator, the method comprising the steps of:
   providing pressure support to the patient;
   determining the patient's spontaneous breathing rate;
   inputting values for a predetermined patient breath rate range and a predetermined minute volume;
   measuring the patient minute volume;
   comparing the patient's breath rate to the predetermined breath rate range;
   comparing the patient's minute volume to the predetermined minute volume; and adjusting pressure support in response thereto.

* * * * *